(12) United States Patent
Sundermann et al.

(10) Patent No.: US 7,214,708 B2
(45) Date of Patent: May 8, 2007

(54) SYNTHETIC DISCODERMOLIDE ANALOGS

(75) Inventors: Kurt F. Sundermann, Burlingame, CA (US); Simon James Shaw, San Francisco, CA (US); Daniel V. Santi, San Francisco, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 0 days.

(21) Appl. No.: 11/261,686

(22) Filed: Oct. 28, 2005

(65) Prior Publication Data

US 2006/0106094 A1 May 18, 2006

Related U.S. Application Data

(60) Provisional application No. 60/629,401, filed on Nov. 18, 2004, provisional application No. 60/629,518, filed on Nov. 18, 2004, provisional application No. 60/629,519, filed on Nov. 18, 2004, provisional application No. 60/629,520, filed on Nov. 18, 2004.

(51) Int. Cl.
- A01N 43/16 (2006.01)
- A61K 31/35 (2006.01)
- C07D 309/00 (2006.01)
- C07D 407/00 (2006.01)
- C07D 309/30 (2006.01)

(52) U.S. Cl. ............ 514/459; 514/471; 549/273; 549/292; 549/321

(58) Field of Classification Search ............ 549/273, 549/292, 321; 514/459, 471
See application file for complete search history.

(56) References Cited

U.S. PATENT DOCUMENTS

| | | | |
|---|---|---|---|
| 4,939,168 A | 7/1990 | Gunasekera | |
| 5,789,605 A | 8/1998 | Smith, III | |
| 5,840,750 A | 11/1998 | Longley | |
| 6,031,133 A | 2/2000 | Smith, III | |
| 6,096,904 A | 8/2000 | Smith, III | |
| 6,127,406 A | 10/2000 | Gunasekera | |
| 6,242,616 B1 | 6/2001 | Smith, III | |
| 6,495,594 B2 * | 12/2002 | Gunasekera et al. | 514/459 |
| 6,506,910 B1 | 1/2003 | Kinder, Jr. | |
| 6,734,177 B2 | 5/2004 | Kinder, Jr. | |
| 2001/0049387 A1 | 12/2001 | Gunasekera | |
| 2002/0103387 A1 | 8/2002 | Smith, III | |
| 2003/0087934 A1 | 5/2003 | Kinder, Jr. | |
| 2003/0153601 A1 | 8/2003 | Kinder, Jr. | |
| 2004/0018598 A1 | 1/2004 | Santi | |
| 2004/0048894 A1 | 3/2004 | Smith, III | |
| 2004/0073049 A1 | 4/2004 | Koch | |
| 2005/0049414 A1 | 3/2005 | Smith, III | |
| 2005/0197369 A1 | 9/2005 | Myles | |

FOREIGN PATENT DOCUMENTS

WO WO 02/12220 A2 2/2002
WO WO 03/080567 A2 10/2003

OTHER PUBLICATIONS

Dermer et al., Bio/Technology, "Another anniversary for the war on cancer", 1994, vol. 12, p. 320.*
Freshney et al., Culture of Animal Cells, A Manual of Basic Technique, Alan R. Liss, Inc., 1983, New York, P4.*
Martelo et al., Chemistry & Biology, "The relationship between Taxol and (+)-discodermolide: sunthetic analogs and modeling studies",2001, vol. 8, pp. 843-855.*
Curran et al., Org. Lett. 4 (13), 2233-2235 (2002), "Simultaneous Preparation of Four Truncated Analogs of Discodermolide by Fluorous Mixture Synthesis".
Gunasekera et al., J. Nat. Prod. 64 (2), 171-174 (2001), "Acetylated Analogues of the Microtubule Stabilizing Agent Discodermolide: Preparation and Biological Activity".
Gunasekera et al., J. Nat. Prod. 65 (11), 1643-1648 (2002), "Five New Discodermolide Analogs from the Marine Sponge Discodermia Species".
Gunasekera et al., J. Nat. Prod. 65 (12), 1830-1837 (2002), "Semisynthetic Analogues of the Microtubule Stabilizing Agent Discodermolide: Preparation and Biological Activity".
Gunasekera et al., J. Nat. Prod. 67 (5), 749-756 (2004), "Synthetic Analogues of the Microtubule Stabilizing Agent (+)-Discodermolide: Preparation and Biological Activity".
Harried et al., J. Org. Chem., 62, 6098-6099 (1997), "Total Synthesis of (−)-Discodermolide: An Application of a Chelation-Controlled Alkylation Reaction".

(Continued)

Primary Examiner—Margaret D. Seaman
Assistant Examiner—Niloofar Rahmani
(74) Attorney, Agent, or Firm—Yuan Chao

(57) ABSTRACT

Synthetic discodermolide analogs having utility as antiproliferative agents, having a structure represented by formula A (A)

Figure 1:
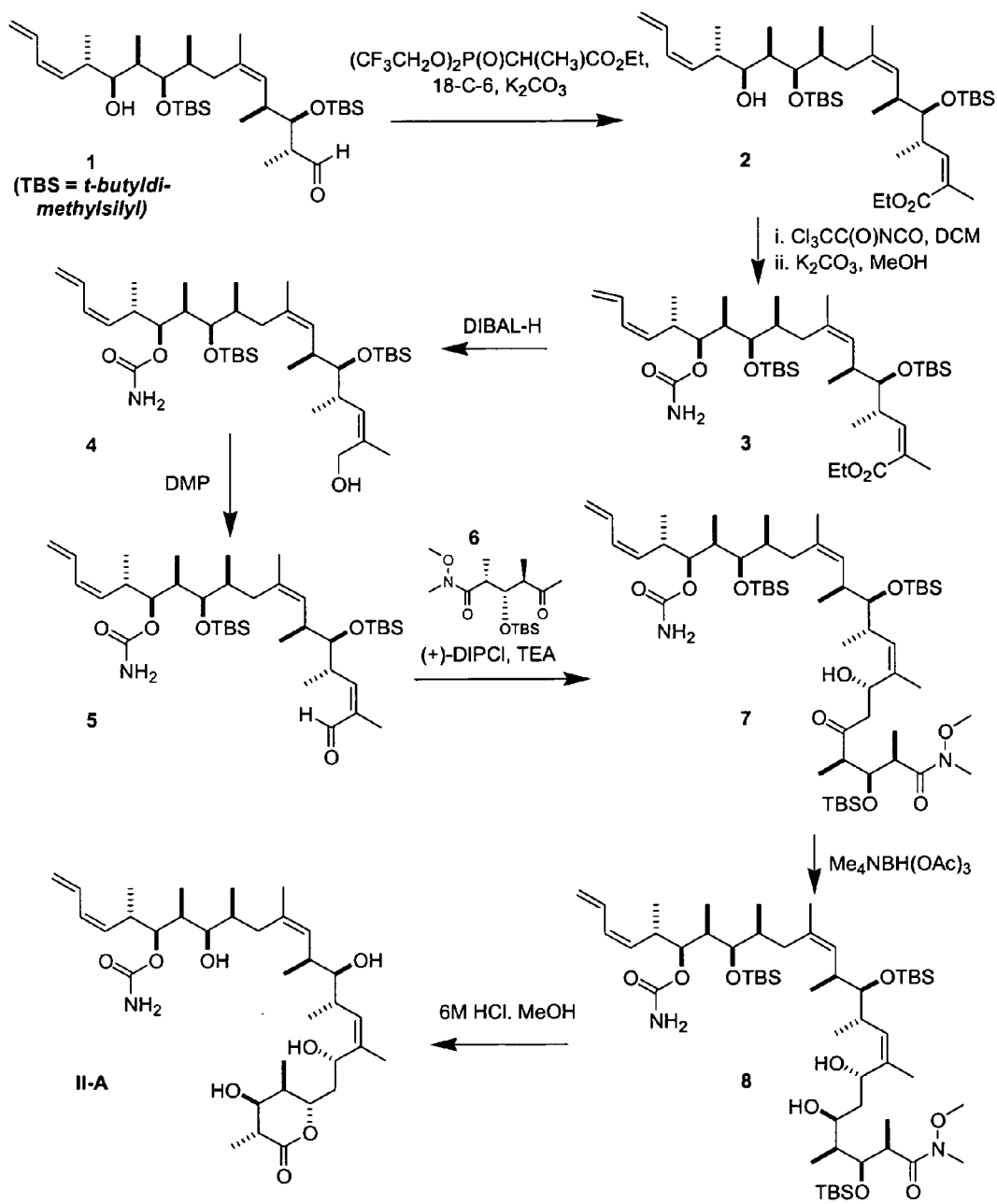

where $R^A$ through $R^E$ and $X^A$ are as defined herein.

20 Claims, 6 Drawing Sheets

OTHER PUBLICATIONS

Harried et al., *J. Org. Chem.*, 68 (17), 6646-6660 (2003), "Total Synthesis of the Potent Microtubule-Stabilizing Agent (+)-Discodermolide".

Hung et al., *J. Am. Chem. Soc.*, 118, 11054-11080 (1996), "Syntheses of Discodermolides Useful for Investigating Microtubule Binding and Stabilization".

Marshall et al., *J. Org. Chem.*, 63, 7885-7892 (1998), "Total Synthesis of (+)-Discodermolide".

Martello et al., *Chem. Biol.* 8, 843-855 (2001), The Relationship between Taxol and (+)-Discodermolide: Synthetic Analogs and Modeling Studies.

Mickel et al., *Org. Proc. Res. Dev.* 8 (1), 92-100 (2004), "Large-Scale Synthesis of the Anti-Cancer Marine Natural Product (+)-Discodermolide. Part 1: Synthetic Strategy and Preparation of a Common Precursor".

Mickel et al., *Org. Proc. Res. Dev.* 8 (1), 101-106 (2004), "Large-Scale Synthesis of the Anti-Cancer Marine Natural Product (+)-Discodermolide. Part 2: Synthesis of Fragments $C_{1-6}$ and $C_{9-14}$".

Mickel et al., *Org. Proc. Res. Dev.* 8 (1), 107-112 (2004), "Large-Scale Synthesis of the Anti-Cancer Marine Natural Product (+)-Discodermolide. Part 3: Synthesis of Fragment $C_{51-21}$".

Mickel et al., *Org. Proc. Res. Dev.* 8 (1), 113-121 (2004), "Large-Scale Synthesis of the Anti-Cancer Marine Natural Product (+)-Discodermolide. Part 4: Preparation of Fragment $C_{7-24}$".

Mickel et al., *Org. Proc. Res. Dev.* 8 (1), 122-130 (2004), "Large-Scale Synthesis of the Anti-Cancer Marine Natural Product (+)-Discodermolide. Part 5: Linkage of Fragments $C_{1-6}$ and $C_{7-24}$ and Finale".

Minguez et al., *Bioorg. Med. Chem.* 11 (15), 3335 (2003), "Synthesis and Biological Assessment of Simplified Analogues of the Potent Microtubule Stabilizer (+)-Discodermolide" (abstract).

Nerenberg et al., *J. Am. Chem. Soc.* 115, 12621-12622 (1993), "Total Synthesis of the Immunosuppressive Agent (−)-Discodermolide".

Paterson et al., *Angew. Chem. Int. Ed.*, 39, 377-380 (2000), "Total Synthesis of the Antimicrotubule Agent (+)-Discodermolide Using Boron-Mediated Aldol Reactions of Chiral Ketones".

Paterson et al., *Eur. J. Org. Chem.*, 12, 2193-2208 (2003), "The Development of a Practical Total Synthesis of Discodermolide, a Promising Microtubule-Stabilizing Anticancer Agent".

Paterson et al., *J. Am. Chem. Soc.*, 123, 9535-9544 (2001), "A Practical Synthesis of (+)-Discodermolide and Analogues: Fragment Union by Complex Aldol Reactions".

Paterson et al., *Org. Lett.*, 5, 35-38 (2003), "1,6-Asymmetric Induction in Boron-Mediated Aldol Reactions: Application to a Practical Total Synthesis of (+)-Discodermolide".

Paterson et al., *Tetrahedron Lett.*, 41, 6935-6939 (2000), "Synthesis of (+)-discodermolide and analogues by control of asymmetric induction in aldol reactions of γ-chiral and (Z)-enals".

Paterson et al., *Tetrahedron Lett.*, 44 (49), 8877 (2003), "Synthesis of Novel Discodermolide Analogues with Modified Hydrogen-Bonding Donor/Acceptor Sites" (abstract).

Smith, III et al., *J. Am. Chem. Soc.*, 112, 8654-8664 (2000), "Evolution of a Gram-Scale Synthesis of (+)-Discodermolide".

Smith, III et al., *J. Am. Chem. Soc.*, 117, 12011-12012 (1995), "Total Synthesis of (−)-Discodermolide".

Smith, III et al., *Org. Lett.* 5 (23), 4405-4408 (2003), "A Practical Improvement, Enhancing the Large-Scale Synthesis of (+)-Discodermolide: a Third-Generation Approach".

Smith, III et al., *Org. Lett.*, 1, 1823-1826 (1999), "Gram-Scale Synthesis of (+)-Discodermolide" (additions and corrections *Org. Lett.* 2, 1983 (2000).

Wermuth, "Designing Prodrugs and Bioprecursors," in Wermuth, ed., *The Practice of Medicinal Chemistry*, 2nd Ed., pp. 561-586 (Academic Press 2003).

He et al., *Drug Discovery Today* 2001, 6 (22), 1153-1164, "Novel molecules that interact with microtubules and have a functional activity similar to Taxol™".

Paterson et al., *Org. Lett.* 2004, 6 (26), 4933-4936, Total Synthesis of (+)-Discodermolide: An Improved Endgame Exploiting a Still-Gennari-Type Olefination with a C1-C8 β-Ketophosphonate Fragment.

* cited by examiner

TBS = t-butyldimethysilyl
PMP = p-methoxyphenyl
PMB = p-methoxybenzyl

TBS = *t*-butyldimethylsilyl

SYNTHETIC DISCODERMOLIDE ANALOGS

CROSS-REFERENCE TO RELATED APPLICATIONS

This application claims the benefit under 35 U.S.C. §119 (e) of U.S. Provisional Applications Nos. 60/629,401; 60/629,518; 60/629,519; 60/629,520; each filed Nov. 18, 2004; the disclosures of which are incorporated herein by reference.

BACKGROUND OF THE INVENTION

1. Field of the Invention

This invention relates to discodermolide compounds and methods for their making and use.

2. Description of Related Art (+)-Discodermolide (hereinafter "discodermolide") is a polyketide natural product isolated from the marine sponge *Discodermia dissoluta* (Gunasekera et al., U.S. Pat. No. 4,939,168 (1990) and U.S. Pat. No. 5,840,750 (1998)). It is a potent inhibitor of tumor cell growth, acting via a microtubule stabilization mechanism, and has entered phase I clinical trials as an anti-cancer agent.

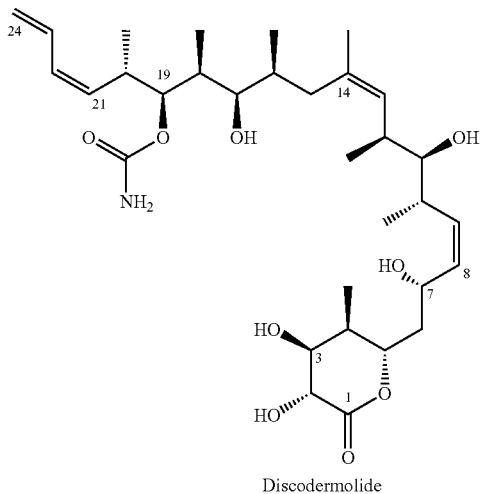

Discodermolide

The supply of discodermolide from natural sources is meager, because the sponge usually inhabits depths where it is harvestable only by submersible vehicles and produces discodermolide in very low concentrations. It is believed that the actual producing organism is a microbial symbiont inside the sponge and not the sponge itself, but efforts to isolate and culture the symbiont have been unsuccessful. Consequently, the availability of discodermolide for clinical trials and research is dependent on material made by chemical synthesis. To date, at least six different total syntheses of discodermolide have been reported: (1) Smith, III et al., *J. Am. Chem. Soc.*, 117, 12011 (1995); Smith, III et al., *Org. Lett.*, 1, 1823 (1999) (additions and corrections *Org. Lett.* 2, 1983 (2000)); Smith, III et al., *J. Am. Chem. Soc.*, 112, 8654 (2000); Smith, III et al., *Org. Lett.* 5 (23), 4405–4408 (2003); (2) Mickel et al., *Org. Proc. Res. Dev.* 8 (1), 92 (2004); Mickel et al., *Org. Proc. Res. Dev.* 8 (1), 101(2004); Mickel et al., *Org. Proc. Res. Dev.* 8 (1), 107 (2004); Mickel et al., *Org. Proc. Res. Dev.* 8 (1), 113 (2004); Mickel et al., *Org. Proc. Res. Dev.* 8 (1), 122 (2004); (3) Paterson et al., *Angew. Chem. Int. Ed.*, 39, 377 (2000); Paterson et al., *Tetrahedron Lett.*, 41, 6935 (2000); Paterson et al., *J. Am. Chem. Soc.*, 123, 9535–9544 (2001); Paterson et al., *Org. Lett.*, 5, 35 (2003); (4) Harried et al., *J. Org. Chem.*, 62, 6098 (1997); Harried et al., *J. Org. Chem.*, 68 (17), 6646–6660 (2003); (5) Nerenberg et al., *J. Am. Chem. Soc.* 115, 12621 (1993); Hung et al., *J. Am. Chem. Soc.*, 118, 11054–11080 (1996); and (6) Marshall et al., *J. Org. Chem.*, 63, 7885 (1998); the disclosures of which are incorporated herein by reference.

A review of the various syntheses has been published: Paterson et al., *Eur. J. Org. Chem.*, 12, 2193 (2003). Additionally, many partial syntheses have been reported for one discodermolide synthon or another.

Besides discodermolide itself, many structurally related compounds ("discodermolide compounds") are known. Some are less abundant congeners isolated from *D. dissoluta*. Others are by-products or model compounds from one of the aforementioned syntheses. Yet others are the result of efforts to provide an easier-to-synthesize (i.e., less expensive) discodermolide compound or a discodermolide compound having a better spectrum of properties compared to discodermolide itself (which has been reported to produce certain adverse effects). Disclosures relating to discodermolide compounds include: Smith, III et al., U.S. Pat. No. 5,789,605 (1998); Longley et al., U.S. Pat. No. 5,840,750 (1998); Smith, III et al., U.S. Pat. No. 6,031,133 (2000); Smith, III et al., U.S. Pat. No. 6,096,904 (2000); Gunasekera et al., U.S. Pat. No. 6,127,406 (2000); Smith, III et al., U.S. Pat. No. 6,242,616 B1 (2001); Gunasekera et al., U.S. Pat. No. 6,495,594 B2 (2002); Kinder, Jr., U.S. Pat. No. 6,506,910 B1 (2003); Kinder, Jr. et al., U.S. Pat. No. 6,734,177 B2 (2004); Gunasekera et al., US 2001/0049387 A1 (2001); Smith, III et al., US 2002/0103387 A1 (2002); Kinder, Jr. et al., US 2003/0087934 A1 (2003); Kinder, Jr. et al., US 2003/0153601 A1 (2003); Santi et al., US 2004/0018598 A1 (2004); Smith, III et al., US 2004/0048894 A1 (2004); Koch et al., US 2004/0073049 A1 (2004); Kinder, Jr. et al., WO 02/12220 A2 (2002); Chen et al., WO 03/080567 A2 (2003); Martello et al., *Chem. Biol.* 8, 843–855 (2001); Gunasekera et al., *J. Nat. Prod.* 64 (2), 171–174 (2001); Curran et al., *Org. Lett.* 4 (13), 2233–2235 (2002); Gunasekera et al., *J. Nat. Prod.* 65 (11), 1643–1648 (2002); Gunasekera et al., *J. Nat. Prod.* 65 (12), 1830–1837 (2002); Minguez et al., *Bioorg. Med. Chem.* 11 (15), 3335–3357 (2003); Paterson et al., *Tetrahedron Lett.*, 44 (49), 8877–8882 (2003); and Gunasekera et al., *J. Nat. Prod.* 67 (5), 749–756 (2004); the disclosures of which are incorporated herein by reference.

However, a discodermolide compound having a balance between the positive attributes of discodermolide but without its negative ones has not yet been developed. The present invention provides new discodermolide analogs having attractive activity profiles.

BRIEF SUMMARY OF THE INVENTION

In one embodiment, there is provided a compound having a structure represented by formula A:

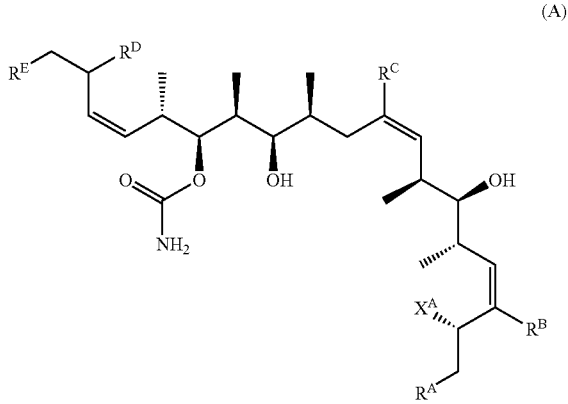

(A)

and the pharmaceutically acceptable salts, esters, solvates, hydrates, and prodrugs thereof wherein $R^A$ is

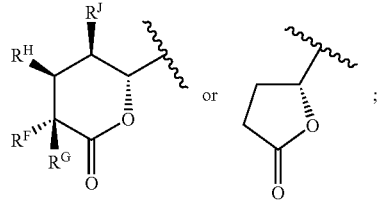

wherein $R^F$ and $R^J$ are independently H or $CH_3$;

$R^G$ is H;

$R^H$ is H, $OCH_3$, or OH, or $R^H$ combines with $R^G$ to form a bond;

$R^B$ and $R^C$ are independently H or $CH_3$;

$R^D$ and $R^E$ are each H or $R^D$ and $R^E$ combine to form a bond; and $X^A$ is H or $CH_3(OCH_2CH_2)_nOCH_2O$, where the subscript n is 0 or 1;

subject to the proviso that at least one of the following conditions is satisfied:

(a) $R^B$ is $CH_3$;

(b) $X^A$ is $CH_3(OCH_2CH_2)_nOCH_2O$, where the subscript n is 0 or 1; or (c) $R^A$ is

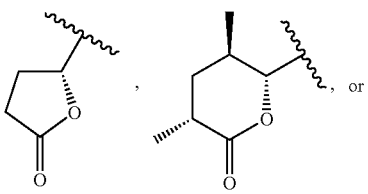

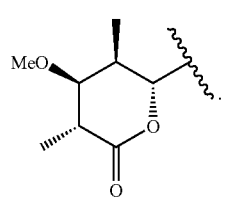

In another embodiment, there is provided a compound having a structure represented by formula I:

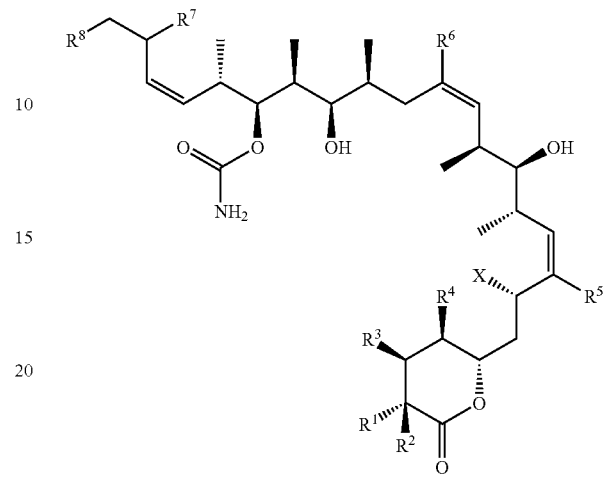

and the pharmaceutically acceptable esters, solvates, hydrates, and prodrugs thereof wherein $R^1$, $R^4$, $R^5$, and $R^6$ are independently H or $CH_3$;

$R^2$ is H;

$R^3$ is H or OH, or $R^3$ combines with $R^2$ to form a bond;

$R^7$ and $R^8$ are each H or $R^7$ and $R^8$ combine to form a bond; and

X is $CH_3(OCH_2CH_2)_nOCH_2O$, where the subscript n is 0 or 1.

In another embodiment, there is provided a compound having a structure represented by formula II:

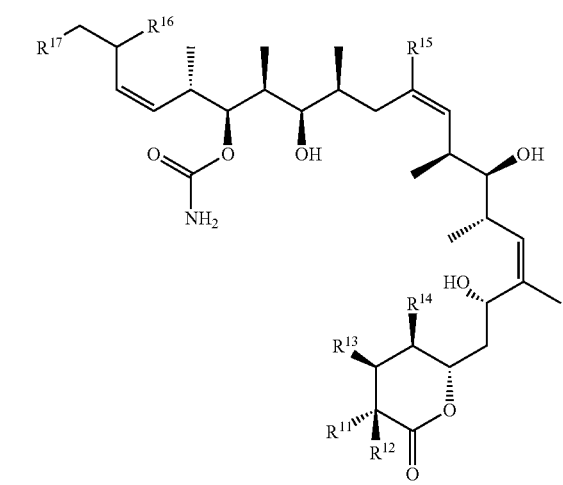

and the pharmaceutically acceptable esters, solvates, hydrates, and prodrugs thereof wherein
$R^{11}$, $R^{14}$, and $R^{15}$ are independently H or $CH_3$;
$R^{12}$ is H;
$R^{13}$ is H or OH, or $R^{13}$ combines with $R^{12}$ to form a bond; and
$R^{16}$ and $R^{17}$ are each H or $R^{16}$ and $R^{17}$ combine to form a bond.

In one embodiment, there is provided a compound having a structure represented by formula III:

(III)

and the pharmaceutically acceptable esters, solvates, hydrates, and prodrugs thereof wherein
$R^{21}$ and $R^{22}$ are independently H or $CH_3$; and
$R^{23}$ and $R^{24}$ are each H or $R^{23}$ and $R^{24}$ combine to form a bond.

In another embodiment, there is provided a compound having a structure represented by formula IV:

(IV)

and the pharmaceutically acceptable salts, esters, solvates, hydrates, and prodrugs thereof wherein
$R^{31}$ is

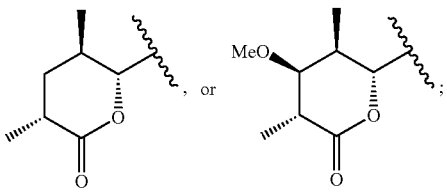

$R^{32}$ and $R^{33}$ are independently H or $CH_3$; and
$R^{34}$ and $R^{35}$ are each H or $R^{34}$ and $R^{35}$ combine to form a bond.

In another embodiment, this invention provides a method of inhibiting the proliferation of a target cell, comprising contacting the target cell with an effective amount of a compound of this invention.

In another embodiment, this invention provides a method of treating a hyperproliferative disease, comprising administering to a patient suffering from such hyperproliferative disease a therapeutically effective amount of a compound of this invention.

In another embodiment, this invention provides for the use of a compound of this invention for the preparation of a medicament for treating a hyperproliferative disease.

BRIEF DESCRIPTION OF THE DRAWING(S)

Figure 5:
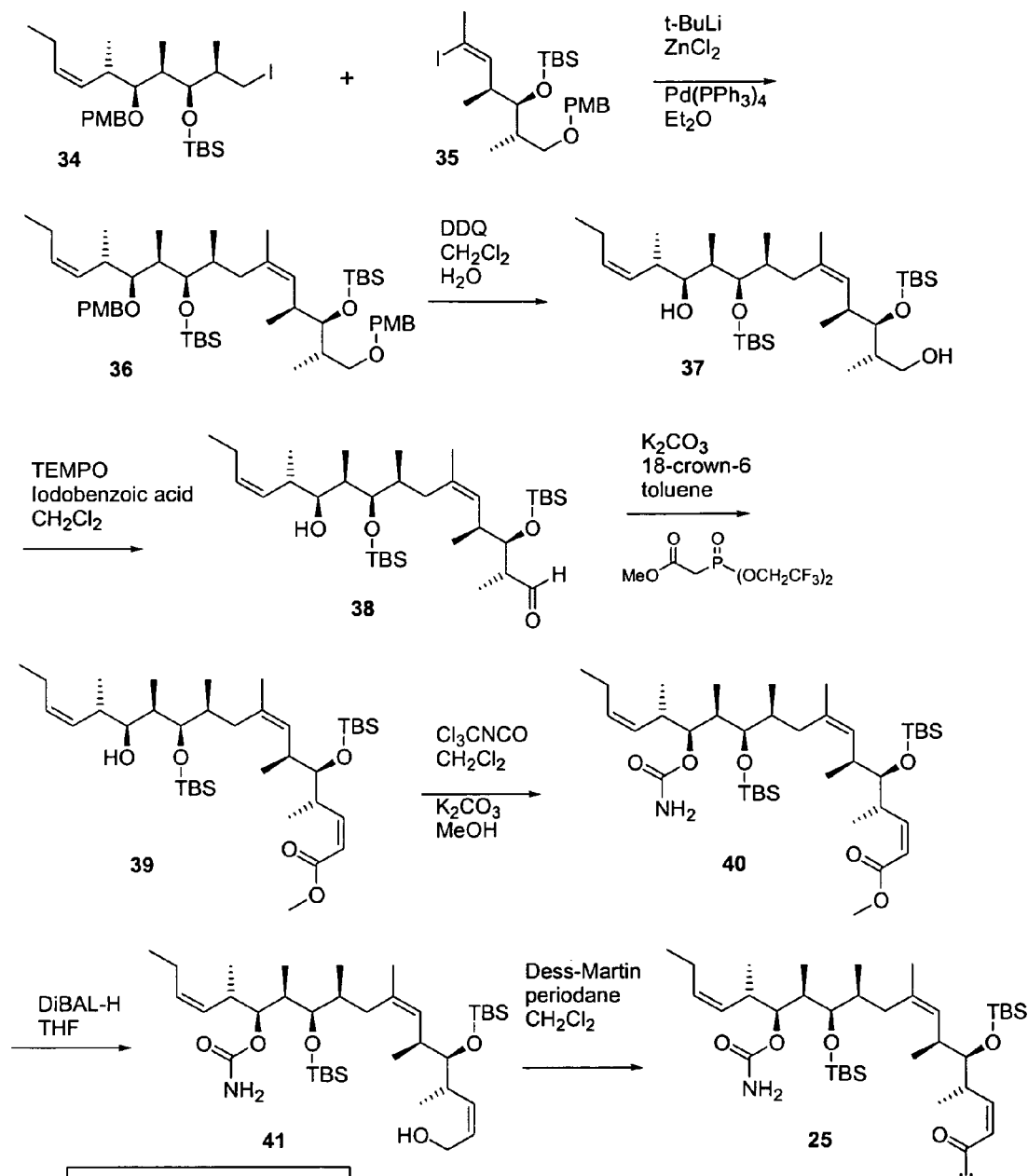
Figure 6:
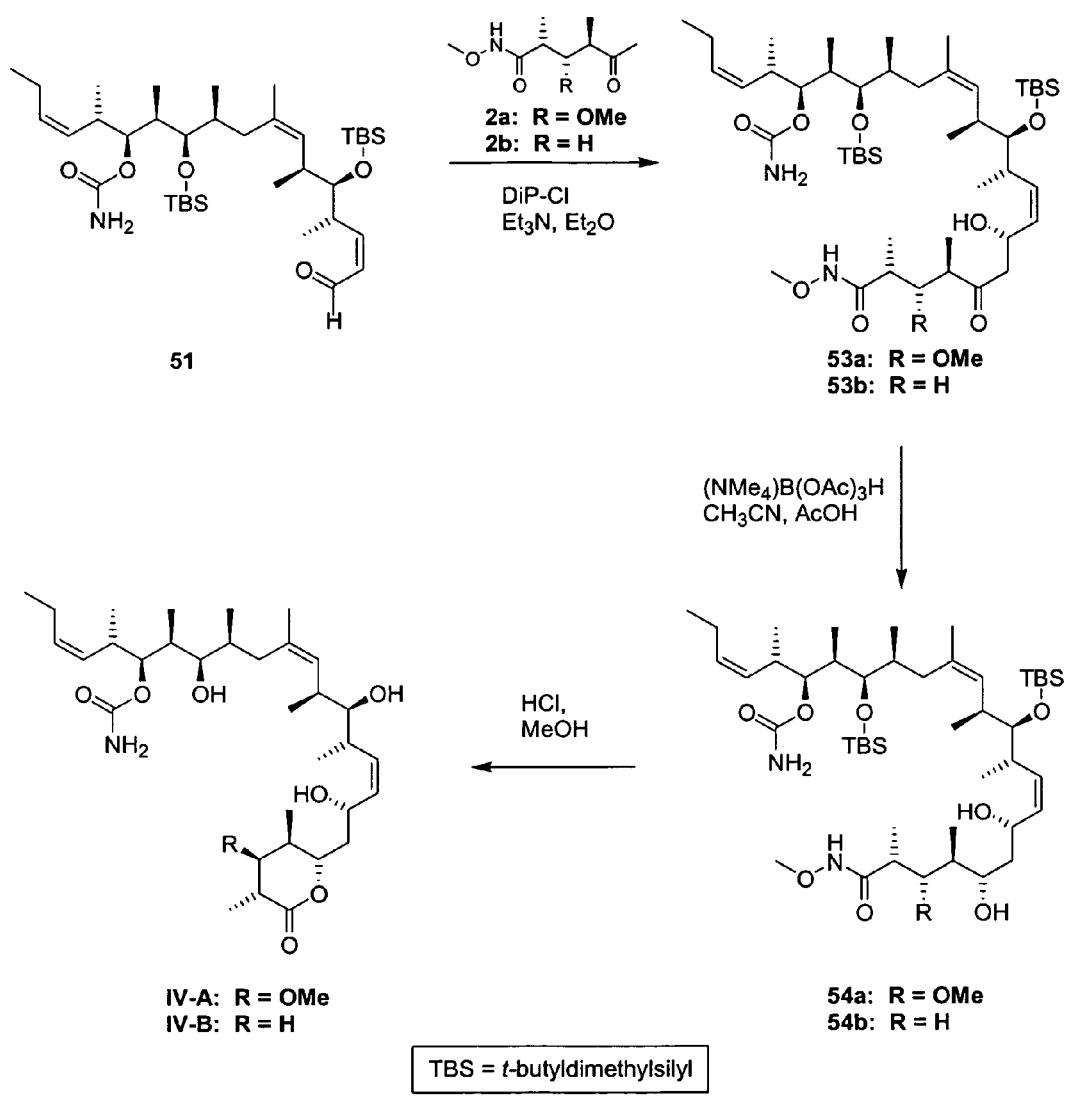

FIG. 1 shows a scheme for the synthesis of compounds II.
FIGS. 2, 3, 4, and 5 show schemes relating to the synthesis of compounds III and/or IV.
FIG. 6 shows a scheme relating to the synthesis of compounds IV.

DETAILED DESCRIPTION OF THE INVENTION

Definitions

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenyl-cyclohexylamine salt, benzathine salt, sodium salt, tetramethylammonium salt, and the like.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

Compounds and Methods

In a preferred embodiment, $R^1$ and $R^4$ are $CH_3$, $R^2$ and $R^5$ are H, $R^3$ is OH, and $R^7$ and $R^8$ combine to form a bond, corresponding to a compound represented by formula Ia:

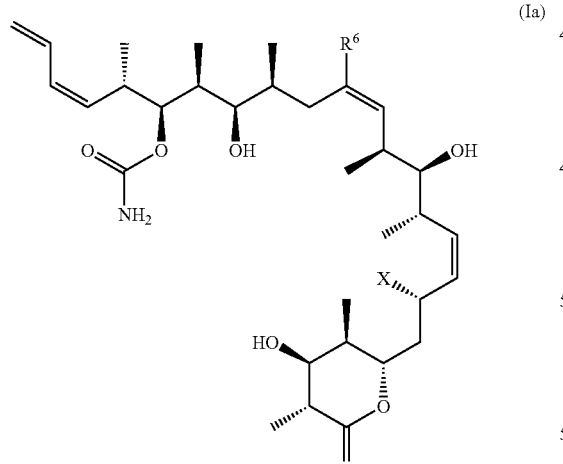
(Ia)

In another preferred embodiment of compounds I, $R^1$, $R^4$, and $R^6$ are $CH_3$, $R^2$ and $R^5$ are H, $R^3$ is OH, and $R^7$ and $R^8$ combine to form a bond, corresponding to a compound represented by formula Ib:

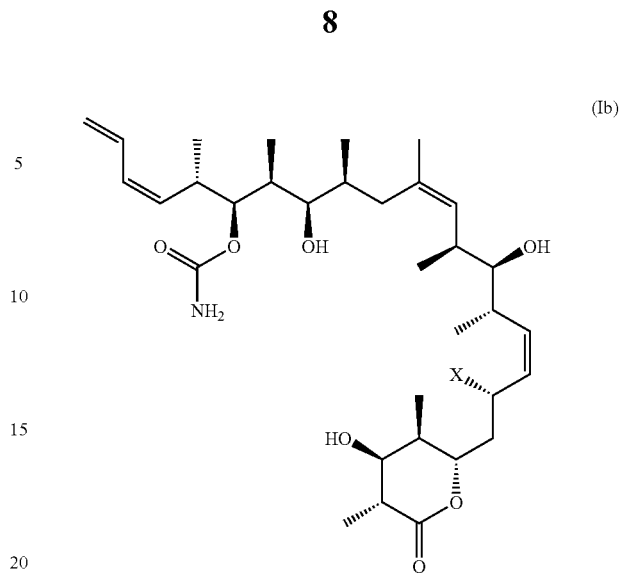
(Ib)

Examples of compounds I include compounds I-A, I-B, and I-C:

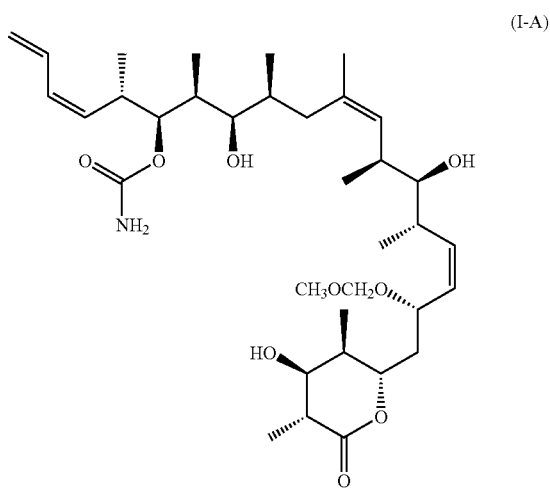
(I-A)

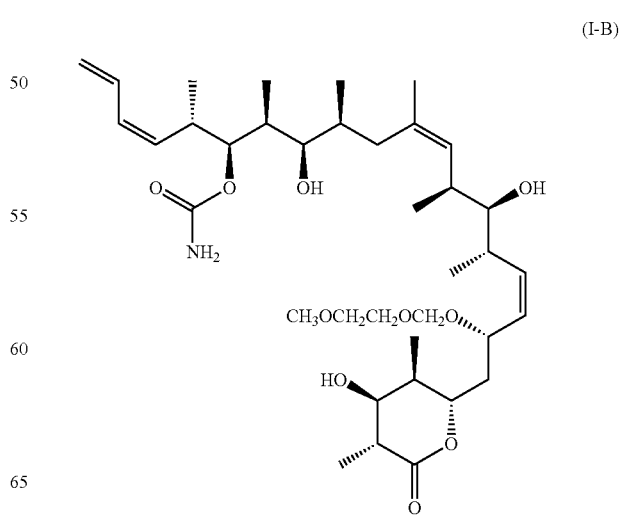
(I-B)

(I-C)

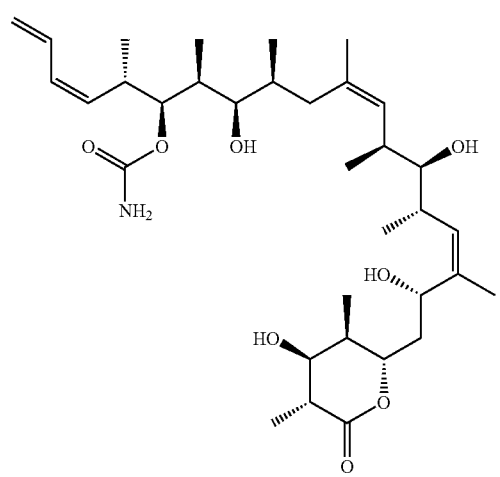

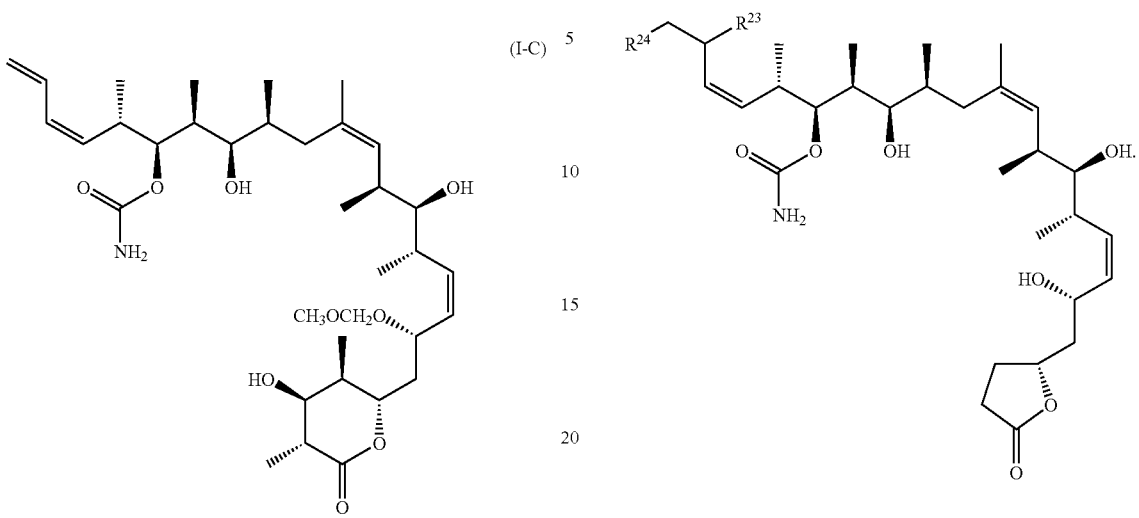

Examples of compounds III are compounds III-A and III-B:

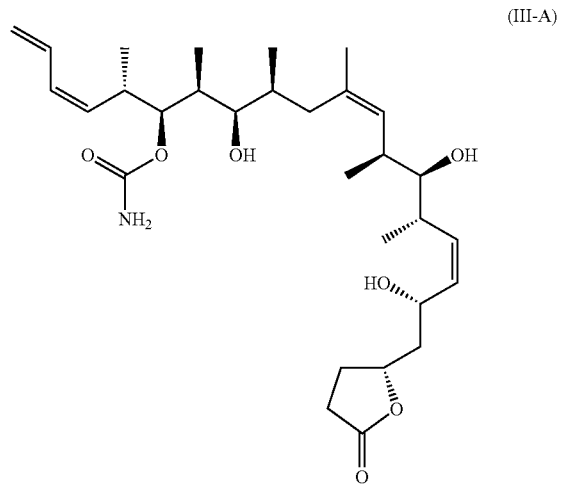

In a preferred embodiment of compounds II, $R^{11}$, $R^{14}$, and $R^{15}$ are $CH_3$, $R^{12}$ is H, $R^{13}$ is OH, and $R^{16}$ and $R^{17}$ combine to form a bond, corresponding to a compound represented by formula II-A (8-methyldiscodermolide):

(II-A)

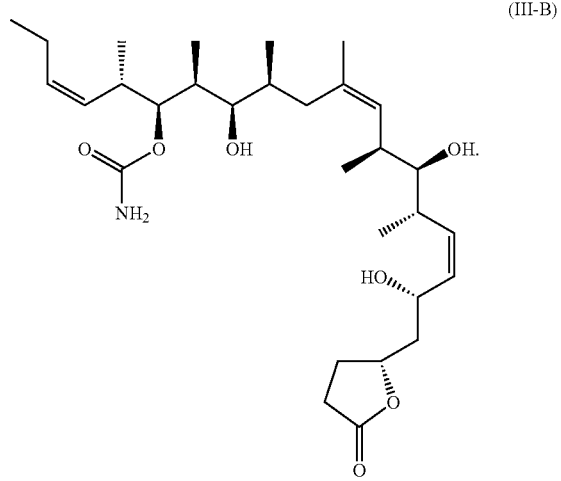

In a preferred embodiment of compounds III, $R^{21}$ is H and $R^{22}$ is $CH_3$, corresponding to a compound of structure IIIa:

In a preferred embodiment of compounds IV, $R^{32}$ is OH, $R^{33}$ is $CH_3$, corresponding to a compound represented by formula IVa:

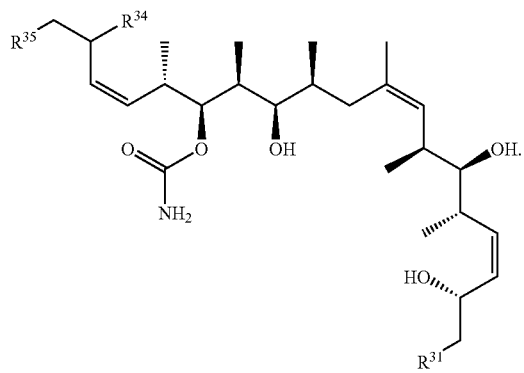

(IVa)

Preferred compounds according to formulae IV include compounds IV-A and IV-B:

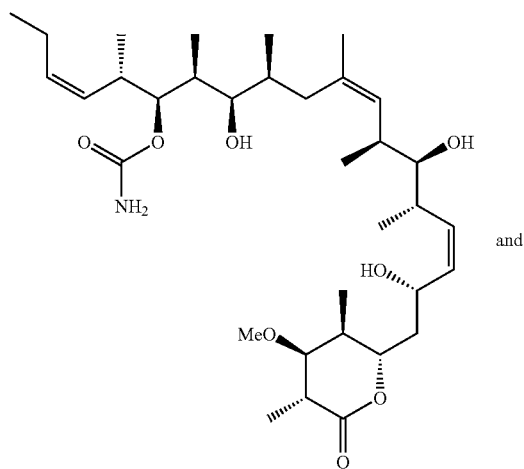

(IV-A)

and

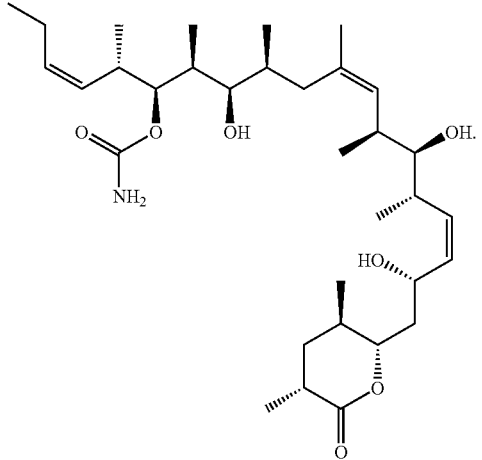

(IV-B)

The present invention also includes methods for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary.

The methods and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved. Thus, the compositions described herein can be combined with other treatment modalities, such as surgery and/or radiation. In some embodiments of the present invention, an agent or procedure is further included to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol.

Compounds of this invention can be administered in combination with other anti-cancer or cytotoxic agents, including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bortezomib, busulfan, calicheamycin, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino17-demethoxygeldanamycin (17-DMAG), gemcitabine, hydroxy-urea, imatinib, interferons, interleukins, irinotecan, leptomycin B, maytansine, methotrexate, mitomycin C, oxaliplatin, paclitaxel, spongistatins, suberoylanilide hydroxamic acid (SAHA), thiotepa, topotecan, trichostatin A, vinblastine, vincristine, and vindesine.

In particular, the co-administered anti-cancer or cytotoxic agent can be a protein kinase inhibitor, including: quinazolines, particularly 4-anilinoquinazolines such as Iressa (AstraZeneca; N-(3-chloro-4-fluorophenyl)-7-methoxy-6-[3-(4-morpholinyl)propoxy]-4-quinazolinamine) and Tarceva (Roche/Genentech; N-(3-ethynylphenyl)-6,7bis(2-methoxyethoxy)-4-quinazolinamine monohydrochloride); phenylamino-pyrimidines such as Gleevec (Novartis; 4-[(4-methyl-1-piperazinyl)methyl]-N-[4-methyl-3-[[4-(3-pyridinyl)-2-pyrimidinyl]amino]phenyl]benzamide); pyrrolo- and pyrazolopyrimidines such as BIBX 1382 (Boehringer Ingelheim; N8-(3-chloro-4-fluorophenyl)-N-2-(1-methyl-4-piperidinyl)-pyrimido[5,4-d]pyrimidine-2,8-diamine); indoles and oxindoles such as Semaxinib (Pharmacia; 3-[(3,5-dimethyl-1H-pyrrol-2-yl)methylene]-1, 3-dihydro-2H-Indol-2-one); benzylidene malononitriles; flavones such as flavopiridol (Aventis; 2-(2-chlorophenyl)-5,7-dihydroxy-8-[(3S,4R)-3-hydroxy-1-methyl-4-piperidinyl]-4H-1-benzopyran-4-one); staurosporines such as CEP-701 (Cephalon); antibodies such as Herceptin (Genentech); and ribozymes such as Angiozyme (Ribozyme Pharmaceuticals).

In another aspect of the present invention, non-cancer disorders that are characterized by cellular hyperproliferation are treated. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis. irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

For human administration, an effective amount of a compound of this invention is used, optionally in combination with a pharmaceutically acceptable carrier. The composition may be dry, or it may be a solution. Treatment may be reactive, for treating an existing condition, or prophylactic, to forestall development of a condition. Compounds of this invention can be used in the preparation of a medicament. The compounds may be administered orally, topically, or parenterally (e.g., intravenously, subcutaneously, intraperitoneally, transdermally).

Compounds of this invention may be used in a pharmaceutical formulation comprising a compound of this invention and an excipient. Excipients that may be used include carriers, surface active agents, thickening or emulsifying agents, solid binders, is dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003), the disclosure of which is incorporated herein by reference.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemistry,* 2nd Ed., pp. 561–586 (Academic Press 2003). Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

The practice of this invention can be further understood by reference to the following examples, which are provided by way of illustration and not of limitation.

EXAMPLE 1

The synthesis of compound I-A is shown by the following reaction:

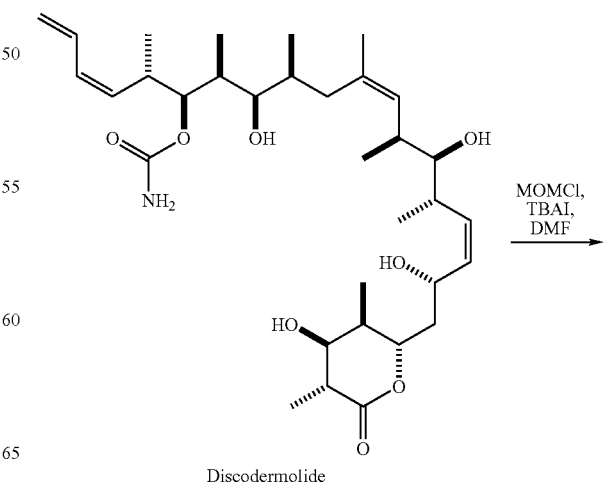

Discodermolide

-continued

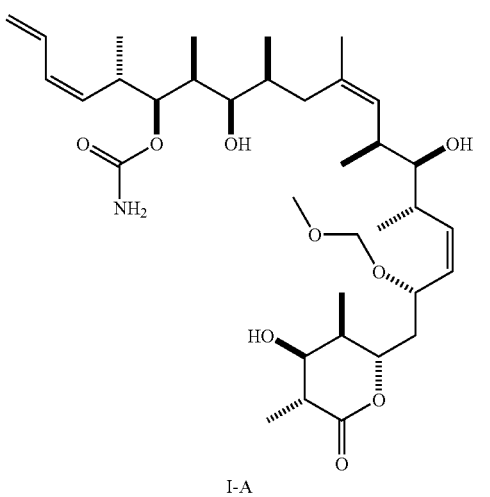

I-A

To a stirred solution of discodermolide (15 mg, 0.026 mmol) in N,N-dimethylformamide ("DMF", 0.2 mL) at room temperature ("RT") was added diisopropylethylamine, (0.11 mL), tetrabutylammonium iodide ("TBAI", 1 mg, 0.003 mmol), and chloromethyl methyl ether ("MOMCl", 0.01 mL, 0.13 mmol). After 5 h, the solution was diluted with EtOAc and sat. aq. NH$_4$Cl was added. The layers were separated and the aqueous layer was extracted with EtOAc. The combined organic extracts were washed with sat. aq. NaHCO$_3$, brine, dried (MgSO$_4$), concentrated in vacuo and purified by flash column chromatography (SiO$_2$, 5–10% MeOH in CH$_2$Cl$_2$) providing 5 mg of compound I-A as a colorless oil (and 7 mg of unreacted discodermolide). $^1$H NMR (400 MHz, CDCl$_3$) δH 6.60 (1H, ddd, J=16.8, 10.6, 10.6 Hz), 6.02 (1H, dd, J=11.1, 11.0 Hz), 5.53 (1H, apparent t, J=10.2 Hz), 5.39–5.25 (2H, m), 5.24–5.06 (3H, m), 4.80–4.54 (5H,m), 4.51 (1H, d, J=6.5 Hz) 3.72 (1H, dd, J=4.0, 4.0 Hz), 3.34 (3H, s) 3.26 (1H, dd, J=4.8, 4.3 Hz), 3.21 (1H, dd, J=6.4, 4.8 Hz), 3.00 (1H, ddq, J=9.9, 6.9, 6.9 Hz), 2.72–2.60 (2H,m), 2.60–2.51 (1H, m), 2.10–1.80 (10H, m), 1.69–1.61 (1H, m), 1.61 (3H, s), 1.29 (3H, d, J=7.2 Hz), 1.07 (3H, d, J=7.0 Hz), 1.00 (3H, d, J=6.4 Hz), 0.99 (3H, d, J=6.8 Hz), 0.97 (3H, d, J=6.8 Hz), 0.94 (3H, d, J=6.7 Hz), 0.81 (3H, d, J=5.5 Hz); $^{13}$C NMR (100 MHz, CDCl$_3$) δC 173.8, 157.2, 136.1, 133.5, 132.8, 132.0, 130.2, 129.9, 129.8, 117.9, 93.6, 79.1, 78.8, 77.2, 75.8, 73.0, 67.3, 55.5, 43.0, 39.9, 37.2, 36.1, 36.0, 35.8, 35.0, 34.6, 33.0, 23.2, 17.9, 17.4, 15.4, 15.4, 13.7, 12.5, 8.8; HRMS (CI) calcd for C$_{35}$H$_{61}$O$_9$N [M+H]+ 638.42538, found 638.42626.

EXAMPLE 2

The synthesis of compound I-B is shown by the following reaction:

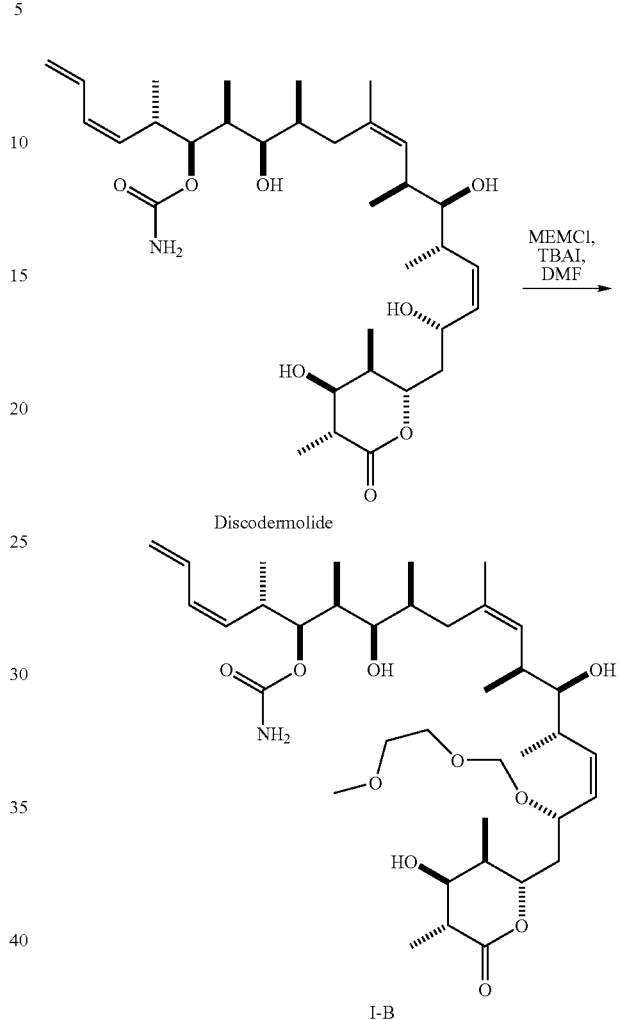

To a stirred solution of discodermolide (12 mg, 0.026 mmol) in DMF (0.25 mL) at RT was added diisopropylethylamine, (0.088 mL), TBAI (1 mg, 0.003 mmol), and 2-methoxyethoxymethyl chloride ("MEMCl", 0.02 mL, 0. mmol). After 8 h, the solution was diluted with EtOAc and sat. aq. NH$_4$Cl was added. The layers were separated and the aqueous layer was extracted with EtOAc. The combined organic extracts were washed with sat. aq. NaHCO$_3$, brine, dried (MgSO$_4$), concentrated in vacuo and purified by flash column chromatography (SiO$_2$, 5–10% MeOH in CH$_2$Cl$_2$) providing 2 mg of compound I-B as a colorless oil. $^1$H NMR (400 MHz, CDCl$_3$) δH 6.60 (1H, ddd, J=17.5, 10.9, 10.9 Hz), 6.02 (1H, dd, J=11.1, 11.0 Hz), 5.53 (1H, apparent t, J=10.3 Hz), 5.39–5.25 (2H, m), 5.24–5.06 (3H, m), 4.81–4.50 (6H,m), 3.79 (1H, dd, J=12.9, 5.6 Hz) 3.72 (1H, dd, J=4.1, 4.1), 3.37–3.50 (3H, m), 3.37 (3H, s) 3.28 (1H, dd, J=4.8, 4.8 Hz), 3.21 (1H, dd, J=6.8, 4.6 Hz), 3.00 (1H, ddq, J=9.4, 6.7, 6.7 Hz), 2.74–2.53 (3H, m), 2.05–1.80 (10H, m), 1.69–1.61 (1H, m), 1.63 (3H, s), 1.31 (3H, d, J=7.2 Hz), 1.07 (3H, d, J=6.9 Hz), 1.01 (3H, d, J=6.4 Hz), 0.99 (3H, d, J=6.8

Hz), 0.97 (3H, d, J=6.8 Hz), 0.95 (3H, d, J=6.7 Hz), 0.82 (3H, d, J=5.5 Hz); HRMS (CI) calcd for $C_{37}H_{64}O_{10}N$ [M+H]+ 682.45302, found 682.45226.

EXAMPLE 3

The synthesis of compound I-C is shown by the following reaction:

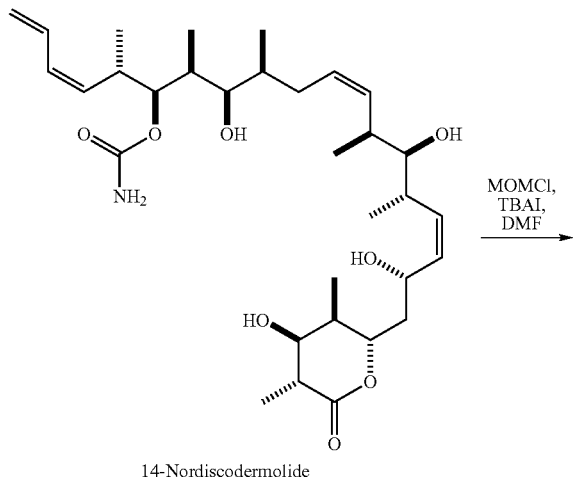

14-Nordiscodermolide

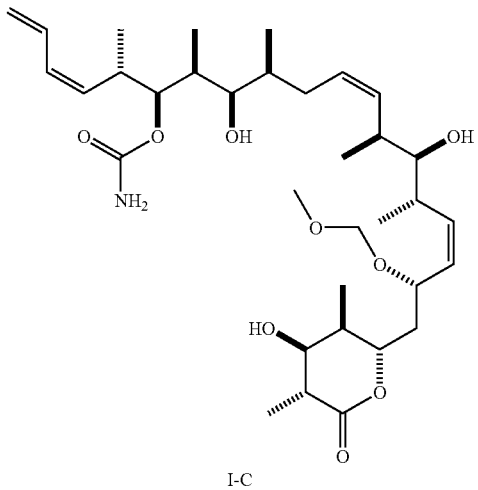

I-C

To a stirred solution of 14-nordiscodermolide (Smith, III et al., US 2004/0048894 A1 (2004), 20 mg, 0.034 mmol) in DMF (0.25 mL) at room temperature was added diisopropylethylamine, (0.15 mL), TBAI (1 mg, 0.003 mmol), and MOMCl (0.02 mL, 0.26 mmol). After 4 h, the solution was diluted with EtOAc and sat. aq. $NH_4Cl$ was added. The layers were separated and the aqueous layer was extracted with EtOAc. The combined organic extracts were washed with sat. aq. $NaHCO_3$, brine, dried ($MgSO_4$), concentrated in vacuo and purified by flash column chromatography ($SiO_2$, 5–10% MeOH in $CH_2Cl_2$) providing 7 mg of compound I-C as a colorless oil $^1$H NMR (400 MHz, $CDCl_3$) δH 6.60 (ddd, 1H, J=10.5 Hz, J=10.5 Hz, J=16.7 Hz), 6.02 (dd, 1H, J=11.0 Hz, J=11.0 Hz), 5.54 (apparent t, 1H, J=10.7 Hz), 5.45–5.16 (m, 5H), 5.12 (d, 1H, J=10.3 Hz), 4.80–4.52 (m, 5H), 4.51 (d, 1H, J=6.6 Hz), 3.72 (dd, 1H, J=4.3 Hz, J=4.0 Hz), 3.37–3.31 (obscured m, 1H), 3.35 (s, 3H), 3.25 (apparent t, 1H, J=5.8 Hz), 2.98 (1H, m), 2.73–2.54 (m, 3H), 2.18–1.74 (m, 10H), 1.74–1.62 (m, 1H), 1.31 (d, 3H, J=7.3 Hz), 1.07 (d, 3H, J=6.9 Hz), 1.01 (d, 3H, J=6.7 Hz), 0.99 (d, 3H, J=6.8 Hz), 0.98 (d, 3H, J=6.8 Hz), 0.97 (d, 3H, J=6.5 Hz), 0.87 (d, 3H, J=6.5 Hz); $^{13}$C NMR (100 MHz, $CD_3CN$) δC 173.6, 157.2, 134.9, 117.9 (obscured), 133.9, 133.5, 132.3, 129.7, 129.4, 127.3, 92.9, 78.2, 78.0, 76.6, 74.4, 72.0, 66.5, 54.5, 42.9, 39.6, 37.4, 35.8, 35.5, 35.4, 35.2, 33.9, 31.1, 17.8, 17.1, 15.6, 14.7, 14.5, 12.1, 8.3; HRMS (CI) calcd for $C_{34}H_{58}O_9N$ [M+H]+ 624.41116, found 624.41224.

Those skilled in the art will appreciate that other compounds I of this invention can be made by generally following the methods described in the preceding examples, mutatis mutandis. Compounds in which the $C_{23}$–$C_{24}$ double bond is hydrogenated (i.e., $R^7$ and $R^8$ are each H) can be made by selective hydrogenation, as disclosed in Gunasekera et al., U.S. Pat. No. 4,939,168 (1990), the disclosure of which is incorporated herein by reference. The preparation of compounds I where $R^1$, $R^2$, $R^3$, and $R^4$ are other than as in discodermolide proper can be achieved by adaptation of the general methodology of the various published total syntheses of discodermolide and also of the procedures in Smith, III et al., U.S. Pat. No. 5,789,605 (1998); Smith, III et al., U.S. Pat. No. 6,096,904 (2000); Smith, III et al., U.S. Pat. No. 6,242,616 B1 (2001); Smith, III et al., US 2002/0103387 A1 (2002); and Smith, III et al., US 2004/0048894 A1 (2004).

EXAMPLE 4

The biological activities of compounds I were evaluated by measuring their inhibitory effect on the proliferation of various tumor cell lines. Results, including comparative ones for discodermolide, are tabulated in Table 1. MCF-7, A549, SKOV-3, and CCRF-CEM are human breast cancer, lung cancer, ovary cancer, and leukemia cell lines, respectively. HL-60/MX2 is a leukemia cell line resistant to mitoxantrone. A549 t12 is an A549 subline resistant to paclitaxel. CCRF-CEM/PTX, CCRF-CEM/VBL, and CCRF-CEM/VP16 are CCRF-CEM sublines resistant to paclitaxel, vinblastine, and VP-16 (etoposide), respectively. NCI/ADR (also referred to as NCI/ADR-Res) is a multi-drug resistant human breast cancer cell line.

TABLE 1

| Tumor Cell Line | Compound | | | |
|---|---|---|---|---|
| ($IC_{50}$, nM)* | Discodermolide | I-A | I-B | I-C |
| MCF-7 | 14.1 | 0.92 | 5.5 | 5.9 |
| NCI/ADR | 247 | 57 | 140 | ~1000 |
| A549 | 24.4 | 1.8 | 6.7 | 28 |
| SKOV-3 | 31.7 | 6.1 | — | — |
| HL-60/MX2 | 150 | 2.7 | — | 4.4 |
| A549 t12 | 26.7 | 2.9 | 5.8 | 68 |
| CCRF-CEM | 14.8 | 2.4 | — | 6.5 |
| CCRF-CEM/PTX | 92.8 | 1.6 | — | 368 |
| CCRF-CEM/VBL | 158 | 56 | — | 5,000 |
| CCFR-CEM/VP16 | 53 | 1.6 | — | 25 |

*Some results are the average of multiple runs.

EXAMPLE 5

The preparation of compounds II is illustrated in FIG. 1.

To a solution of 2-[bis-(2,2,2-trifluoroethyl)]-ethoxycarbonyl)ethanephosphonate (117 mg, 0.35 mmol, and 18-crown-6 (280 g, 1.0 mmol) in 6 ml THF was added a 0.5 M solution of potassium hexamethyldisilazide ("KHMDS") in toluene (0.68 mL, 0.34 mmol) at −78° C. After 30 min a solution of aldehyde 1 (70 mg, 0.12 mmol; Mickel et al.,

*Org. Proc. Res. Dev.* 8 (1), 113 (2004); Kinder, Jr., et al., US 2003/0087934 A1 (2003), incorporated herein by reference) in 1 ml THF was added dropwise. The pale yellow reaction mixture was stirred for 1 h at 0° C. and then warmed to room temperature and stirred overnight. The reaction was diluted with Et$_2$O and sat. aq. NH$_4$Cl was added. The layers were separated and the aqueous layer was extracted with EtOAc. The combined organic extracts were washed brine, dried (MgSO$_4$), concentrated in vacuo and purified by flash column chromatography (SiO$_2$, 5% EtOAc/hexanes) providing 40 mg of hydroxy ester 2 as a colorless oil.

To a stirred solution of hydroxy ester 2 (38 mg, 0.057 mmol) in CH$_2$Cl$_2$ at RT was added trichloroacetyl isocyanate (0.07 mL, 0.57 mmol). After 1.5 h, the mixture was concentrated in vacuo, redissolved in MeOH (0.72 mL) and powdered K$_2$CO$_3$ was added at 0° C. The mixture was stirred at RT for 2 h and then partitioned between water and CH$_2$Cl$_2$. The layers were separated and the aqueous layer was extracted with CH$_2$Cl$_2$. The combined organic extracts were washed with sat. aq. NaHCO$_3$, brine, dried (MgSO$_4$), concentrated in vacuo and purified by flash column chromatography (SiO$_2$, 20% EtOAc in hexanes) providing 24 mg of ester 3 as a colorless oil.

To a stirred solution of ester 3 (23 mg, 0.032 mmol) in CH$_2$Cl$_2$ (0.5 mL) at −78° C. was added DIBAL-H (0.26 mL, 0.26 mmol). After 1.5 h the mixture was poured into a solution of sat. aq. sodium potassium tartrate at 0° C. The mixture was stirred for 2 h until clear. The layers were separated and the aqueous layer was extracted with CH$_2$Cl$_2$. The combined organic extracts were washed with sat. aq. NaHCO$_3$, brine, dried (MgSO$_4$), concentrated in vacuo and purified by flash column chromatography (SiO$_2$, 20% EtOAc in Hexanes) providing 22 mg alcohol 4 as a colorless oil.

To a stirred solution of alcohol 4 (22 mg, 0.032 mmol) in CH$_2$Cl$_2$ (0.75 mL) at RT was added Dess-Martin periodinane (21 mg, 0.048 mmol). After 45 min, the resultant suspension was diluted with sat aq NaHCO$_3$ and sat aq Na$_2$S$_2$O$_4$ (1:1) and stirred for 45 min until the mixture was clear. The mixture was extracted with Et$_2$O and the combined organic extracts were washed with sat. aq. NaHCO$_3$, brine, dried (MgSO$_4$), concentrated in vacuo and purified by flash column chromatography (SiO$_2$, 20% EtOAc in Hexanes) providing 21 mg of aldehyde 5 as a colorless oil.

To a stirred solution of (+)-DIPCl in Et$_2$O (0.2 mL) at 0° C. was added TEA (triethylamine) (0.05 mL) followed by a solution of ketone 6 (102.5 mg, 0.31 mmol; Mickel et al., *Org. Proc. Res. Dev.* 8 (1), 101(2004); incorporated herein by reference) in Et$_2$O (0.150 mL). After 2 h, the mixture was cooled to −78° C. and aldehyde 5 (21 mg, 0.031 mmol) in Et$_2$O (0.4 mL) was added. After 2 h at −78° C., the mixture was placed in a −20° C. freezer for 16 h. The reaction was quenched at 0° C. by addition of MeOH (0.4 mL) followed by addition of pH 7 buffer (0.4 mL, 1M) and hydrogen peroxide (0.15 mL, 30% aq.). After stirring for 1 h at room temperature, the mixture was diluted with water and CH$_2$Cl$_2$. The layers were separated and the aqueous layer was extracted with CH$_2$Cl$_2$. The combined organic extracts were washed with sat. aq. NaHCO$_3$, brine, dried (MgSO$_4$), concentrated in vacuo and purified by flash column chromatography (2×, SiO$_2$, 10–20% EtOAc in hexanes) providing 20 mg of ketone 7 as a colorless oil.

To a stirred solution of Me$_4$NBH(OAc)$_3$ (52.2 mg, 0.19 mmol) in MeCN (0.21 mL) was added AcOH (0.21 mL) at RT. After 30 min, the solution was cooled to −30° C. and ketone 7 in MeCN (0.41 mL) and AcOH (0.41 mL) was added. The solution was stirred for 30 min at −30° C. and then for additional 2 h at 0° C., before the addition of sat. aq. sodium potassium tartrate. After 10 min, the suspension was diluted with CH$_2$Cl$_2$ and sat aq NaHCO$_3$ was slowly added. The layers were separated and the aqueous layer was extracted with CH$_2$Cl$_2$. The combined organic extracts were washed with sat. aq. NaHCO$_3$, brine, dried (MgSO$_4$), concentrated in vacuo and purified by flash column chromatography (SiO$_2$, 25% EtOAc in hexanes) providing 12 mg of diol 8 as a colorless oil.

To a stirred solution of diol 8 (12 mg, 0.012 mmol) in MeOH (0.6 mL) at RT was added 0.1 mL of 6N HCl. After 4 h, 0.1 mL of 6N HCl was added followed by an additional 0.1 mL after 16 h. After a further 8 h, the reaction was partitioned between sat. aq. NaHCO$_3$ and CH$_2$Cl$_2$. The layers were separated and the aqueous layer was extracted with CH$_2$Cl$_2$. The combined organic extracts were washed with sat. aq. NaHCO$_3$, brine, dried (MgSO$_4$), concentrated in vacuo and purified by flash column chromatography (SiO$_2$, 5–10% MeOH in CH$_2$Cl$_2$) providing 4 mg of compound II-A as a colorless oil. $^1$H NMR (400 MHz, CDCl$_3$) δH 6.61 (1H, ddd, J=16.8, 10.6, 10.6 Hz), 6.03 (1H, dd, J=10.6.1, 10.6 Hz), 5.35 (1H, apparent t, J=10.8 Hz), 5.2 (2H, m), 5.12 (1H, d, J=9.9 Hz, H$_{13}$), 5.11 (1H, d, J=9.5 Hz), 4.71 (4H, m), 4.61 (1H, apparent t, J=10.0 Hz), 3.73 (1H, dd, J=3.5, 3.5 Hz), 3.28 (1H, dd, J=4.0, 3.9 Hz), 3.14 (1H, dd, J=7.6, 4.3 Hz), 2.99 (1H, ddq, J=9.9, 6.9, 6.9 Hz), 2.82 (1H, ddq, J=9.8, 6.8, 6.8 Hz), 2,70 (1H, dq, J=7.3, 4.6 Hz), 2.64–2.57 (1H, m), 2.10–1.84 (10H, m), 1.73 (3H, s) 1.70–1.67 (1H, m), 1.64 (3H, s), 1.31 (3H, d, J=7.2 Hz), 1.08 (3H, d, J=7.0 Hz), 1.02 (3H, d, J=6.2 Hz), 1.00 (3H, d, J=6.0 Hz), 0.99 (3H, d, J=6.3 Hz), 0.94 (3H, d, J=6.8), 0.83 (3H, d, J=5.4 Hz); $^{13}$C NMR (100 MHz, CD$_3$CN) δC 173.7, 157.3, 137.3, 133.4, 132.3, 130.4, 129.4, 127.9 117.9, 78.7, 78.2, 76.9, 75.0, 72.2, 64.6, 43.1, 38.7, 37.4, 35.4, 35.2, 34.8, 33.8, 33.2, 22.3, 18.3, 17.6, 17.1, 16.0, 14.8, 14.2, 12.1, 8.2; HRMS (ES+) calcd for C$_{34}$H$_{58}$O$_8$N [M+H]+ 608.41973, found 608.41570.

Those skilled in the art will appreciate that other compounds II can be made by generally following the method previously described, *mutatis mutandis*. For instance, compounds in which R$^{15}$ is H can be made by using, as a starting material, counterparts of compounds 1 where the corresponding CH$_3$ has been replaced by H. The preparation of discodermolide compounds and intermediates therefor where such a replacement has been effected is disclosed in Smith, III, et al., US 2004/0048894 A1 (2004), the disclosure of which is incorporated herein by reference. Compounds in which the C$_{23}$–C$_{24}$ double bond is hydrogenated (i.e., R$^{16}$ and R$^{17}$ are each H) can be made by selective hydrogenation, as disclosed in Gunasekera et al., U.S. Pat. No. 4,939,168 (1990), the disclosure of which is incorporated herein by reference. The preparation of compounds II where R$^{11}$, R$^{12}$, R$^{13}$, and R$^{14}$ are other than as in discodermolide proper can be achieved by adaptation of the general methodology of the various published total syntheses of discodermolide and also of the procedures in Smith, III et al., U.S. Pat. No. 5,789,605 (1998); Smith, III et al., U.S. Pat. No. 6,096,904 (2000); Smith, III et al., U.S. Pat. No. 6,242,616 B1 (2001); Smith, III et al., US 2002/0103387 A1 (2002); and Smith, III et al., US 2004/0048894 A1 (2004).

EXAMPLE 6

The biological activity of compound II-A was evaluated by measuring its inhibitory effect on the proliferation of various tumor cell lines. Results, including comparative ones for discodermolide, are tabulated in Table 2. (The

TABLE 2

| Tumor Cell Line | Compound | |
|---|---|---|
| (IC$_{50}$, nM)* | Discodermolide | II-A |
| MCF-7 | 14.1 | 7.7 |
| NCI/ADR | 247 | 610 |
| A549 | 24.4 | 12 |
| SKOV-3 | 31.7 | 29 |
| HL-60/MX2 | 150 | 11 |
| A549 t12 | 26.7 | 31 |
| CCRF-CEM | 14.8 | 5.6 |
| CCRF-CEM/PTX | 92.8 | 42.3 |
| CCRF-CEM/VBL | 158 | 152 |
| CCFR-CEM/VP16 | 53 | 9 |

*Some results are the average of multiple runs.

EXAMPLE 7

Figure 2:
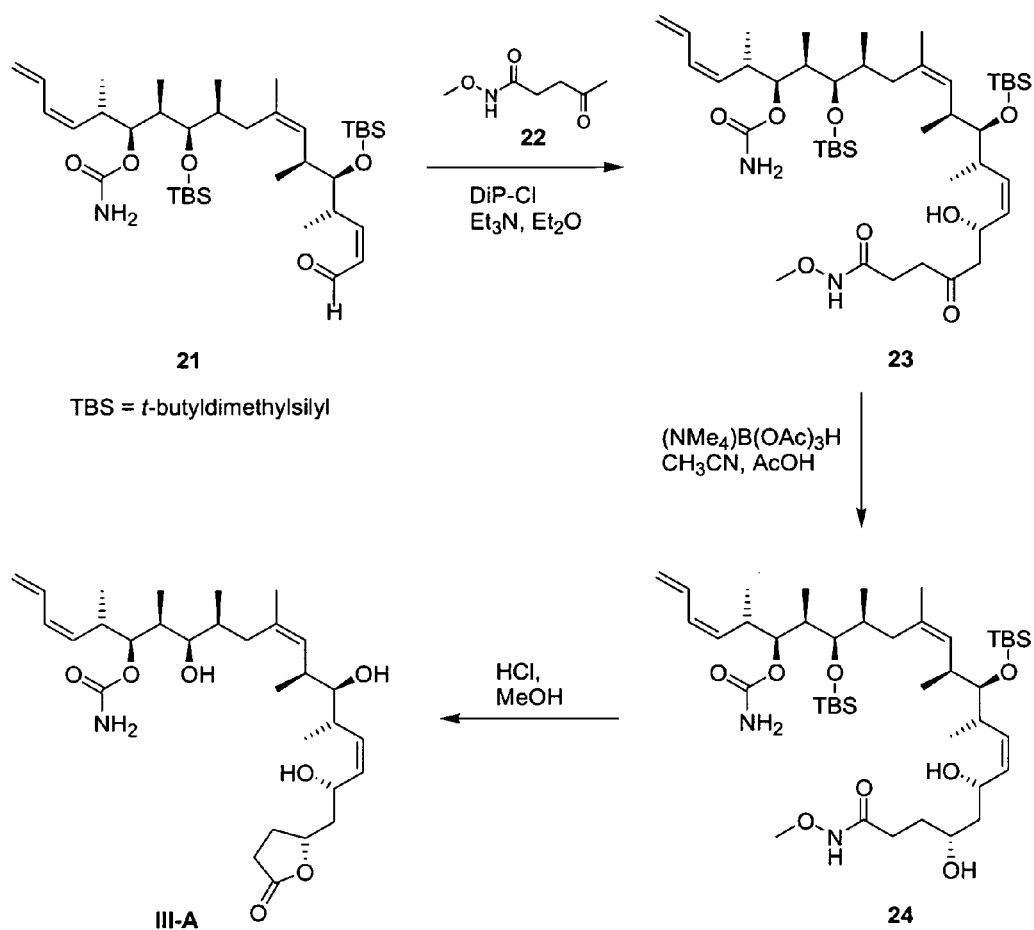
Figure 3:
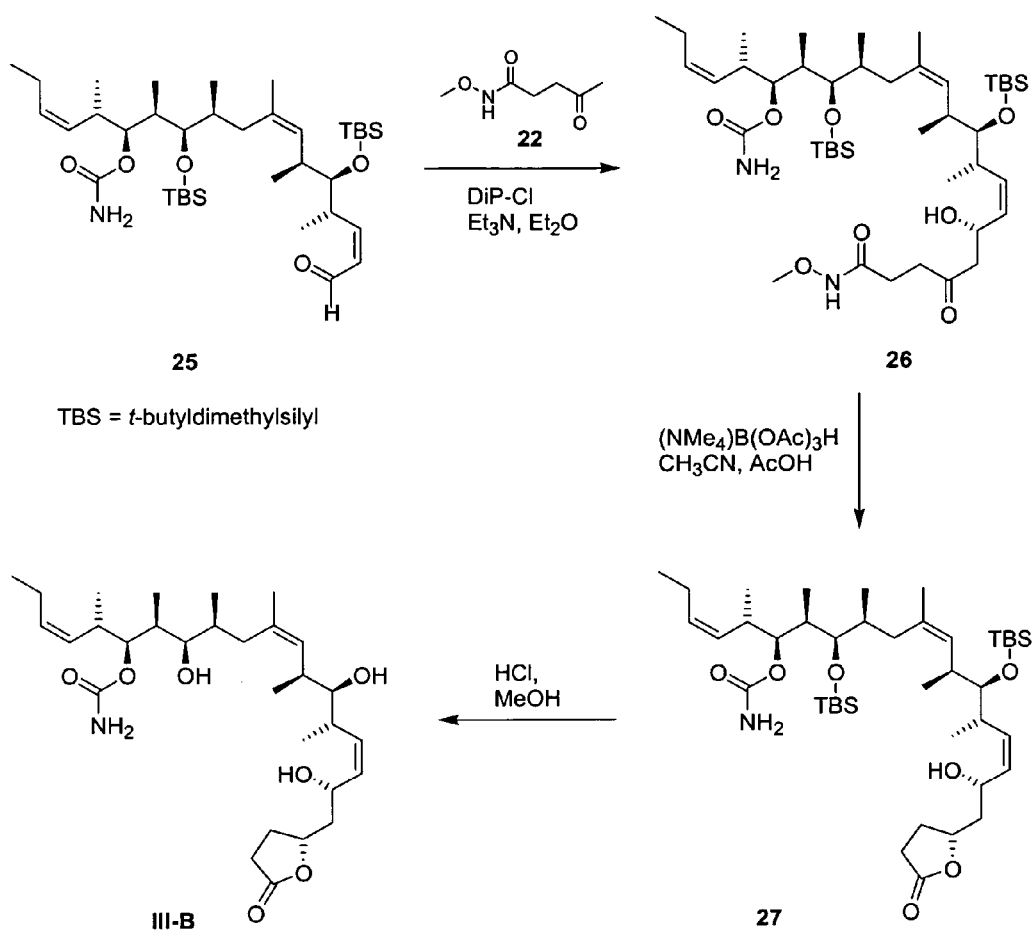

Standard procedures for certain steps used in common in the synthetic schemes of FIG. 2 or FIG. 3 in relation to the synthesis of compounds III are described following.

Diastereoselective aldol reaction. To a solution of diisopinocamphylene boron chloride (8.0 eq, "DiP-Cl") in diethyl ether at 0° C. was added triethylamine (8.8 eq), forming a milky solution to which was added a solution of levulinic acid Weinreb amide 22 (8.0 eq) in ether. After stirring at 0° C. for 1 hour the solution was cooled to −78° C. and a solution of aldehyde 21 (Mickel et al., Org. Proc. Res. Dev. 8 (1), 113 (2004); incorporated herein by reference) or 25 (1.0 eq) was added as a solution in ether. The solution was stirred at −78° C. for 3 hours and placed at −20° C. for 16 hours. After warming to 0° C., MeOH was added followed by phosphate buffer (pH 7, 1.0 M solution) and hydrogen peroxide (30% solution in water). The mixture was stirred at room temperature for 1 hour before diluting with water and extracting the organics with CH$_2$Cl$_2$ (3×). The combined organic phases were dried (Na$_2$SO$_4$) and concentrated under reduced pressure. Column chromatography (silica) yielded β-hydroxyketone 23 or 26.

Diastereoselective reduction. To a solution of the tetramethylammonium triacetoxyborohydride (10.0 eq) in acetonitrile was added glacial acetic acid. After stirring at room temperature for 30 minutes, the solution was cooled to −30° C. and a pre-cooled solution of β-hydroxyketone 23 or 26 (1.0 eq) in acetonitrile-acetic acid (1:1) was added. The solution was stirred at −30° C. for 30 minutes and then at 0° C. for a further 1 hour before adding a solution of Rochelle's salt and stirring for 5 minutes. The mixture was partitioned between NaHCO$_3$ and CH$_2$Cl$_2$ and the aqueous phase extracted with CH$_2$Cl$_2$ (3×). The combined organic phases were dried (Na$_2$SO$_4$) and concentrated under reduced pressure, affording disilyl ether 24 or 27.

Final deprotection. To a solution of the disilyl ether 24 or 27 (1.0 eq) in MeOH at room temperature was added HCl (4.5M, 2 aliquots) over a period of 60 minutes. After stirring at room temperature for a further 2 hours, the solution was diluted with CH$_2$Cl$_2$ and neutralized with NaHCO$_3$. The aqueous phase was extracted with CH$_2$Cl$_2$ (3×) and the combined organic phases dried (Na$_2$SO$_4$) and concentrated under reduced pressure. Column chromatography (silica) yielded the discodermolide compound III-A or III-B.

EXAMPLE 8

Compound III-A was made according to the scheme shown in FIG. 2.

β-Hydroxyketone 23 was made according to the "Diastereoselective aldol reaction" standard procedure from aldehyde 1 (Mickel et al., Org. Proc. Res. Dev. 8 (1), 113 (2004); Mickel et al., Org. Proc. Res. Dev. 8 (1), 122 (2004); Kinder, Jr., et al., U.S. Pat. No. 6,506,910 B1 (2003); all incorporated herein by reference) and levulinic acid Weinreb amide 22 on a 0.196 mmol scale. The crude product, which was contaminated with starting amide and was a mixture of diastereomers at the 7-position, was taken onto the next step without characterization.

Using the "Diastereoselective reduction" standard procedure on a 0.196 mmol scale, β-hydroxyketone 23 was converted to anti diol 24 (0.110 g, 68% over two steps) as a colorless oil, isolated after column chromatography (silica); $^1$H NMR (400 MHz) δ 6.60 (1H, dt, J 17.0, 10.5 Hz, H-23), 6.03 (1H, dd, J 11.0, 10.5 Hz, H-22), 5.49 (2H, m, H-9, H-8), 5.35 (1H, dd, J 11.0, 10.5 Hz, H-21), 5.21 (1H, d, J 17.0 Hz, H-24trans), 5.12 (1H, d, J 10.0 Hz, H-24cis), 5.01 (1H, d, J 10.0 Hz, H-13), 4.72–4.67 (4H, m, H-19, H-7, NH$_2$), 3.95 (1H, m, H-5), 3.69 (3H, s, NOCH$_3$), 3.37 (1H, dd, J 5.5, 3.5 Hz, H-17), 3.26 (1H, dd, J 7.0, 4.0 Hz, H-11), 3.18 (3H, s, NCH$_3$), 2.97 (1H, dt, J 9.0, 7.0 Hz, H-20), 2.72–2.67 (3H, m, H-10, 2×H-3), 2.42 (1H, dt, J 9.0, 7.0 Hz, H-12), 2.13 (1H, t, J 12.5 Hz, 1×H-15), 1.91–1.87 (2H, m H-18, H-16), 1.82 (2H, q, J 6.5 Hz, 2×H-4), 1.76 (1H, m, 1×H-15), 1.65 (5H, m, H-14', 2×H-6), 0.98 (3H, d, J 7.0 Hz, H-20'), 0.93–0.88 (9H, m, H-18', H-12', H-10'), 0.92 (9H, s, 1×SiC(CH$_3$)$_3$), 0.91 (9H, s, 1×SiC(CH$_3$)$_3$), 0.71 (3H, d, J 7.0 Hz, H-16'), 0.09 (6H, s, 2×SiCH$_3$), 0.05 (3H, s, 1×SiCH$_3$), 0.04 (3H, s, 1×SiCH$_3$); $^{13}$C NMR (100 MHz) δ 157.2 133.8, 133.7, 132.7, 132.2, 132.1, 130.8, 129.7, 117.8, 80.8, 78.5, 76.9, 68.4, 65.6, 61.2, 43.4, 38.2, 36.7, 36.5, 36.4, 34.7, 34.4, 32.1, 31.8, 26.2, 26.2, 22.7, 19.4, 18.5, 17.4, 13.3, 10.1, −2.9, −3.5, −3.5, −3.8; mass spectrum m/z 848 [M+Na]$^+$, 517, 430 (Found: [M+Na]$^+$, 847.5658. C$_{44}$H$_{84}$N$_2$O$_7$Si$_2$ requires [M+Na]$^+$, 847.5659).

Using the "Final deprotection" standard procedure on a 0.072 mmol scale, anti diol 24 was simultaneously deprotected and lactonized, to yield compound III-A (25 mg, 64%) as a colorless oil; $^1$H NMR (400 MHz) δ 6.61 (1H, dt, J 17.0, 10.5 Hz, H-23), 6.03 (1H, t, J 11.0 Hz, H-22), 5.53–5.42 (2H, m, H-9, H-8), 5.36 (1H, t, J 10.5 Hz, H-21), 5.21 (1H, d, J 17.0 Hz, H-24trans), 5.14 (2H, m, H-24cis, H-13), 4.80 (4H, m, H-19, H-5, NH-$_2$), 4.60 (1H, m, H-7), 3.27 (1H, t, J 5.0 Hz, H-17), 3.19 (1H, dd, J 6.5, 5.0 Hz, H-11), 3.00 (1H, dt, J 10.0, 7.0 Hz, H-20), 2.78 (1H, dt, J 9.0, 7.0 Hz, H-10), 2.59–2.52 (2H, m, H-12, 1×H-3), 2.37 (1H, m, 1×H-3), 2.03 (2H, m, 2×H-4), 1.95–1.77 (6H, m, H-18, H-16, 2×H-15, 2×H-6), 1.64 (3H, d, J 1.0 Hz, H-14'), 1.01 (3H, d, J 7.0 Hz, H-10'), 1.01–0.97 (6H, m, H-20', H-18'), 0.94 (3H, d, J 7.0 Hz, H-12'), 0.82 (3H, d, J 5.5 Hz, H-16'); $^{13}$C NMR (100 MHz) δ 177.2, 157.3, 134.6, 133.5, 133.4, 132.5, 129.8, 129.6, 117.9, 78.9, 78.7, 78.0, 75.8, 65.2, 43.2, 37.2, 35.8, 35.2, 34.6, 33.0, 28.8, 28.4, 23.2, 18.4, 17.4, 15.6, 13.8, 8.8; mass spectrum m/z 558 [M+Na]$^+$, 519 (Found: [M+Na]$^+$, 558.3425. C$_{30}$H$_{49}$NO$_7$ requires [M+Na ]$^+$, 558.3401).

EXAMPLE 9

Compound III-B was made according to the scheme shown in FIG. 3.

Using the "Distereoselective aldol reaction" standard procedure, β-hydroxyketone 26 was made from aldehyde 25 and levulinic acid Weinreb amide 22. Crude β-hydroxyketone 26 was obtained as a mixture of diastereomers at the 7-position; $^1$H NMR (400 MHz) δ 5.63 (1H, dd, J 10.5, 10.0 Hz, H-9), 5.40–5.32 (2H, m, H-22, H-8), 5.27 (1H, m, H-21), 4.96 (1H, d, J 10.0 Hz, H-13), 4.75 (1H, m, H-7), 4.70 (1H, m, H-19), 4.66 (2H, m, $NH_2$), 3.73 (3H, s, $NOCH_3$), 3.35 (1H, dd, J 6.5, 3.0 Hz, H-17), 3.25 (1H, dd, J 7.0, 3.0 Hz, H-11), 3.16 (3H, s, $NCH_3$), 2.84–2.57 (6H, m, H-20, H-10, 2×H-6, 2×H-5), 2.37 (1H, m, H-12), 2.17–1.84 (5H, m, 2×H-23, H-18, H-16, 1×H-15), 1.61 (3H, s, H-14'), 1.57 (1H, m, 1×H-15), 1.01–0.88 (15H, m, H-24, H-20', H-18', H-12', H-10'), 0.92 (9H, s, 1×$SiC(CH_3)_3$), 0.90 (9H, s, 1×$SiC(CH_3)_3$), 0.70 (3H, d, J 6.5 Hz, H-16'), 0.09 (3H, s, 1×$SiCH_3$), 0.07 (3H, s, 1×$SiCH_3$), 0.04 (6H, s, 2×$SiCH_3$); mass spectrum m/z 848 [M+Na]$^+$, 675 (Found: [M+Na]$^+$, 847.5699. $C_{44}H_{84}N_2O_8Si_2$ requires [M+Na]$^+$, 847.5659).

The reduction of β-hydroxyketone 26 using the "Diastereoselective reduction" standard procedure on a 0.030 mmol scale occurred with in situ cyclization to 7S-5S lactone 27 (0.005 g, 22%), isolated as a colourless oil after column chromatography (silica); $^1$H NMR (400 MHz) δ 5.52 (1H, t, J 11.0 Hz, H-9), 5.43–5.34 (2H, m, H-22, H-8), 5.26 (1H, dd, J 11.0, 10.5 Hz, H-21), 5.05 (1H, d, J 10.0 Hz, H-13), 4.78 (1H, m, H-5), 4.69 (1H, t, J 5.5 Hz, H-19), 4.56 (3H, m, $NH_2$, H-7), 3.39 (1H, dd, J 5.0, 4.5 Hz, H-17), 3.27 (1H, dd, J 5.5, 5.0 Hz, H-11), 2.82–2.76 (1H, m, H-20), 2.67 (1H, m, H-10), 2.54 (1H, dd, J 9.5, 6.5 Hz, 1×H-3), 2.47–2.32 (2H, m, H-12, 1×H-3), 2.17 (1H, m, 1×H-15), 2.07 (2H, m, 2×H-23,), 1.91–1.86 (4H, m, H-18, H-16, 2×H-4), 1.80–1.74 (3H, m, 1×H-15, 2×H-6), 1.65 (3H, s, H-14'), 0.99–0.91 (15H, m, H-24, H-20', H-18', H-12', H-10'), 0.92 (9H, s, 1×$SiC(CH_3)_3$), 0.91 (9H, s, 1×$SiC(CH_3)_3$), 0.72 (3H, d, J 6.5 Hz, H-16'), 0.09 (3H, s, 1×$SiCH_3$), 0.08 (3H, s, 1×$SiCH_3$), 0.04 (6H, s, 2×$SiCH_3$); $^{13}$C NMR (100 MHz) δ 175.2, 157.0, 135.0, 132.7, 132.1, 132.0, 130.9, 130.5, 80.7, 78.8, 77.9, 64.2, 43.4, 38.0, 36.7, 36.5, 34.9, 33.9, 28.9, 28.5, 26.3, 26.2, 22.8, 20.8, 19.5, 18.5, 17.2, 17.0, 14.4, 13.3, 10.2, −2.8, −3.5, −3.6, −3.8; mass spectrum m/z 789 [M+Na]$^+$ (Found: [M+Na]$^+$, 788.5259. $C_{42}H_{79}NO_7Si_2$ requires [M+Na]$^+$, 788.5287). The 7R-5R lactone was also obtained, as a colourless oil (0.004 g, 17%).

Lactone 27 was deprotected using the "Final deprotection" standard procedure on a 0.065 mmol scale to yield compound III-B (2 mg, 57%) as a colourless oil; $^1$H NMR (400 MHz) δ 5.52 (1H, dd, J 10.5, 7.5 Hz, H-8), 5.49–5.37 (2H, m, H-22, H-9), 5.27 (1H, t, J 10.5 Hz, H-21), 5.17 (1H, d, J 10.0 Hz, H-13), 4.77 (1H, m, H-5), 4.70 (1H, dd, J 6.5, 4.5 Hz, H-19), 4.61 (1H, m, H-7), 3.27 (1H, t, J 5.0 Hz, H-17), 3.20 (1H, dd, J 6.5, 4.5 Hz, H-11), 2.81 (2H, m, H-20, H-10), 2.63–2.58 (1H, m, H-12), 2.54 (1H, dd, J 9.5, 7.0 Hz, 1×H-3), 2.38 (1H, m, 1×H-3), 2.10–2.03 (2H, m, 2×H-23), 1.95–1.81 (8H, m, H-18, H-16, 2×H-15, 2×H-6, 2×H-4), 1.66 (3H, s, H-14'), 1.02 (3H, d, J 7.0 Hz, H-20' or H-10'), 0.99–0.93 (12H, m, H-24, H-18', H-12' and H-20' or H-10'), 0.84 (3H, d, J 6.5 Hz, H-16'); $^{13}$C NMR (100 MHz) δ 177.1, 157.2, 134.7, 133.7, 132.6, 132.3, 130.3, 129.4, 78.9, 77.9, 75.9, 65.3, 43.1, 37.3, 35.9, 35.8, 35.1, 34.1, 33.0, 29.6, 28.7, 28.4, 23.3, 20.7, 18.3, 17.7, 15.5, 14.4, 13.8, 8.9; mass spectrum m/z 560 [M+Na]$^+$, 538 [M+H]$^+$, 560, 459 (Found: [M+Na]$^+$, 560.3578. $C_{30}H_{51}NO_7$ requires [M+Na]$^+$, 560.3558).

EXAMPLE 10

Figure 4:
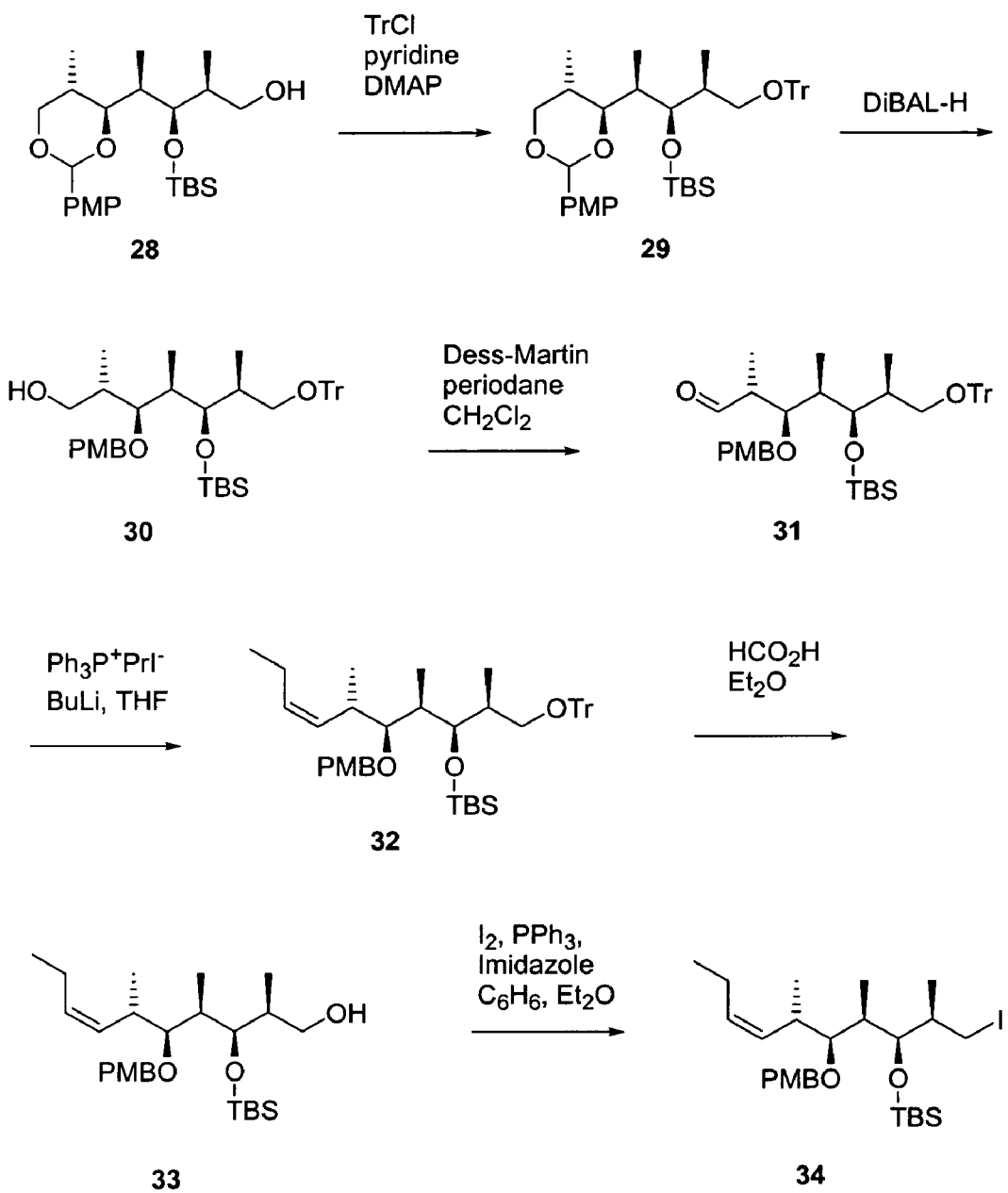

FIG. 4 shows the scheme for the synthesis of alkyl iodide 34 from alcohol 28 (Mickel et al., *Org. Proc. Res. Dev.* 8 (1), 107 (2004); Smith, III et al., U.S. Pat. No. 6,096,904 (2000); incorporated herein by reference), used in the synthesis of aldehyde 25, which in turn is used in the synthesis of compound III-B. FIG. 5 shows the scheme for the synthesis of aldehyde 25 from alkyl iodide 34 and vinyl iodide 35.

To a solution of azeotroped alkyl iodide 34 (1.46 g, 2.54 mmol, 1.0 eq) in ether (11 ml) was added $ZnCl_2$ (2.54 ml of a 1M solution in ether, 1.0 eq). The solution was degassed (freeze-pump-thaw) before cooling to −78° C. tert-Butyllithium (4.48 ml of a 1.7M solution in pentane, 3.0 eq) was added and the solution stirred for 5 minutes before degassing and recharging with nitrogen. The solution was warmed to room temperature and stirred for 1 hour before transferring to an intimate mixture of azeotroped vinyl iodide 35 (1.25 g, 2.41 mmol, 0.95 eq; Smith, III et al., U.S. Pat. No. 6,096,904 (2000); Smith, III et al., U.S. Pat. No. 5,789,605 (1998); incorporated herein by reference) and palladium tetrakis (triphenylphosphine) (0.28 g, 0.25 mmol, 0.1 eq). The mixture was stirred in the dark for 15 hours before quenching with water (20 ml). The organics were extracted with $Et_2O$ (3×30 ml), abd the combined organics washed with $NaHCO_3$ (40 ml) before drying ($Na_2SO_4$) and concentrating under reduced pressure. Column chromatography (silica, 5% EtOAc-hexane) yielded the coupled product 36 (1.50 g, 70%) as a colourless oil; $^1$H NMR (400 MHz) δ 7.29 (2H, d, J 8.5 Hz, 2×m-Ar—H), 7.25 (2H, d, J 9.0 Hz, 2×m-Ar—H), 6.87 (2H, d, J 9.0 Hz, 2×o-Ar—H), 6.86 (2H, d, J 9.0 Hz, 2×o-Ar—H), 5.47 (1H, dd, J 11.0, 10.0 Hz, H-21), 5.37 (1H, m, H-22), 5.00 (1H, d, J 10.0 Hz, H-13), 4.58 and 4.46 (2H, AB system, J 10.5 Hz, 1×$CH_2Ar$), 4.41 and 4.36 (2H, AB system, J 11.5 Hz, 1×$CH_2Ar$), 3.80 and 3.79 (6H, 2s, 2×$OCH_3$), 3.49–3.43 (2H, m, H-17, 1×H-9), 3.38 (1H, dd, J 6.0, 5.5 Hz, H-11), 3.23–3.19 (2H, m, H-19, 1×H-9), 2.48 (1H, m, H-12), 2.13–1.98 (5H, m, H-23, H-18, H-16, 1×H-15), 1.85–1.82 (2H, m, 1×H-15, H-10), 1.56 (3H, s, H-14'), 1.07 (3H, d, J 7.0 Hz, H-20'), 1.01 (3H, d, J 7.0 Hz, H-18'), 1.00–0.88 (9H, m, H-24, H-12', H-10'), 0.96 and 0.89 (18H, 2s, 2×$SiC(CH_3)_3$), 0.74 (3H, d, 7.0 Hz, H-16'), 0.11 and 0.10 (6H, 2s, 2×$Si(CH_3)_2$), 0.03 (6H, s, 2×$Si(CH_3)_2$); $^{13}$C NMR (100 MHz) δ 159.0, 131.8, 131.4, 131.1, 131.1, 131.0, 129.0, 113.6, 84.5, 78.4, 74.8, 72.6, 72.5, 55.2, 39.9, 38.8, 36.2, 35.6, 35.2, 34.8, 26.3, 26.2, 23.0, 21.0, 18.9, 18.6, 18.4, 17.1, 14.5, 10.7, −3.2, −3.3, −3.9.

To a solution of the coupled compound 36 (1.5 g, 1.79 mmol, 1.0 eq) in $CH_2Cl_2$ (30 ml) at 0° C. was added water (3 ml) followed by dichlorodicyanobenzoquinone ("DDQ", 0.9 g, 3.93 mmol, 1.2 eq). The solution was stirred at 0° C. for 30 minutes before partitioning between $CH_2Cl_2$ (60 ml) and $NaHCO_3$ (100 ml). The aqueous phase was extracted with $CH_2Cl_2$ (2×60 ml) and the combined organics washed with $NaHCO_3$ (2×100 ml) before drying ($Na_2SO_4$) and concentrating under reduced pressure. The residue was dissolved in MeOH (15 ml) and $NaBH_4$ (2 spatula) added. After stirring for 10 minutes, $NH_4Cl$ (30 ml) was added and the organic phases extracted with $CH_2Cl_2$ (3×30 ml). The combined organic phases were dried ($Na_2SO_4$) and concentrated under reduced pressure. Column chromatography (silica, 7% EtOAc-hexane) yielded the deprotected diol 37 (0.7 g, 63%) as a colourless oil; $^1$H NMR (400 MHz) δ 5.54 (1H, dt, J 11.00, 7.0 Hz, H-22), 5.18 (1H, t, J 11.0 Hz, H-21), 5.00 (1H, d, J 10.0 Hz, H-13), 3.66 (1H, dd, J 11.0, 4.5 Hz, 1×H-9), 3.61 (1H, dd, J 6.5, 3.0 Hz, H-17), 3.51 (1H, dd, J 11.0, 5.0 Hz, 1×H-9), 3.40 (1H, dd, J 6.5, 4.0 Hz, H-11), 3.26

(1H, dd, 8.5, 3.0 Hz, H-19), 2.63–2.56 (2H, m, H-20, H-12), 2.21 (1H, t, J 12.0 Hz, 1×H-15), 2.11–2.03 (2H, m, 2×H-23), 1.93 (1H, m, H-16), 1.83–1.79 (3H, m, H-18, 1×H-15, H-10), 1.63 (3H, s, H-14'), 0.97 (3H, t, J 7.0 Hz, H-24), 0.95–0.89 (12H, m, H-20', H-18', H-12', H-10'), 0.92 and 0.91 (18H, 2s, 2×SiC(CH$_3$)$_3$), 0.75 (3H, d, J 7.0 Hz, H-16'), 0.09, 0.09, 0.08, 0.07 (3H, s, 1×SiCH$_3$); $^{13}$C NMR (100 MHz) δ 134.1, 133.3, 131.6, 130.3, 81.5, 78.9, 75.6, 65.3, 38.3, 37.9, 37.0, 36.7, 35.8, 34.6, 26.2, 26.1, 23.5, 18.4, 18.3, 17.3, 17.1, 15.8, 14.4, 13.1, 9.6, −3.4, −3.6, −4.0.

To a solution of diol 37 (0.306 g, 0.511 mmol, 1.0 eq) in CH$_2$Cl$_2$ (11 ml), was added iodobenzoic acid (0.454 g, 1.14 mmol, 2.2 eq) followed by TEMPO (0.016 g, 0.10 mmol, 0.2 eq). The solution was stirred at room temperature for 2.5 hours before adding Na$_2$S$_2$O$_3$ (20 ml). The organics were extracted with CH$_2$Cl$_2$ (3×20 ml) and the combined organic phases were washed with NaHCO$_3$ (60 ml) before drying (Na$_2$SO$_4$) and concentration under reduced pressure. Column chromatography (silica, 10% EtOAc-hexane) yielded aldehyde 38 (0.236 g, 77%) as a colourless oil; $^1$H NMR (400 MHz) δ 9.63 (1H, s, CHO), 5.57 (1H, dt, J 11.0, 7.0 Hz, H-22), 5.20 (1H, t, J 10.0 Hz, H-21), 4.83 (1H, d, J 10.5 Hz, H-13), 3.77 (1H, dd, J 7.5, 3.5 Hz, H-11), 3.62 (1H, dd, J 6.5, 6.0 Hz, H-17), 3.27 (1H, d, J 7.0 Hz, H-19), 2.65–2.56 (2H, m, H-20, H-10), 2.52–2.94 (1H, m, H-12), 2.24 (1H, t, J 12.0 Hz, 1×H-15), 2.13–2.05 (2H, m, 2×H-23), 1.93 (1H, m, 1×H-15), 1.80–1.74 (2H, m, H-18, H-16), 1.61 (3H, s, H-14'), 1.08 (3H, d, J 7.0 Hz, H-12'), 1.01–0.88 (9H, m, H-24, H-20', H-10'), 0.93 and 0.90 (18H, 2s, 2×SiC(CH$_3$)$_3$), 0.74 (3H, d, J 7.0 Hz, H-16'), 0.10, 0.09, 0.09, 0.06 (12H, 4s, 4×SiCH$_3$); $^{13}$C NMR (100 MHz) δ 203.2, 135.4, 134.2, 131.5, 129.1, 78.9, 78.3, 75.6, 51.9, 38.0, 37.0, 36.5, 35.8, 34.3, 26.2, 25.9, 23.2, 21.0, 18.4, 18.1, 17.8, 17.1, 14.4, 13.0, 9.7, 9.6, −3.5, −4.2.

Aldehyde 38 was condensed with CH$_3$C(=O)CH$_2$P(=O)(OCH$_2$CF$_3$)$_2$ using K$_2$CO$_3$ in tolune in the presence of 18-crown-6 to yield methyl ester 39.

To a solution of methyl ester 39 (0.300 g, 0.460 mmol, 1.0 eq) in CH$_2$Cl$_2$ (5.0 ml) was added trichloracetyl isocyanate (0.55 ml, 4.601 mmol, 10.0 eq). The solution was stirred at room temperature for 1 hour before concentrating under reduced pressure. The residue was dissolved in methanol (5.0 ml) and cooled to 0° C. before adding ground potassium carbonate (0.500 g) and stirring at 0° C. for 1 hour and room temperature for 1.5 hours. The solution was diluted with water (20 ml) and the organic phases extracted with CH$_2$Cl$_2$ (3×20 ml). The combined organic phases were dried (Na$_2$SO$_4$) and concentrated under reduced pressure. Column chromatography (silica, 10% EtOAc-hexane) yielded carbamoylated methyl ester 40 (0.277 g, 87%) as a pale yellow oil; $^1$H NMR (400 MHz) δ 6.37 (1H, t, J 10.5 Hz, H-9), 5.70 (1H, d, J 11.5 Hz, H-8), 5.41–5.35 (1H, m, H-21), 5.29 (1H, dd, J 11.0, 10.0 Hz, H-20), 4.88 (1H, d, J 10.5 Hz, H-13), 4.72 (2H, br s, NH$_2$), 4.70 (1H, m, H-19), 3.70 (3H, s, OCH$_3$), 3.60 (1H, m, H-10), 3.38 (1H, t, J 4.5 Hz, H-17), 3.34 (1H, t, J 6.0 Hz, H-11), 2.80 (1H, m, H-20), 2.29 (1H, m, H-12), 2.09–1.98 (3H, m, 2×H-23, 1×H-15), 1.88–1.83 (2H, m, H-18, H-16), 1.59–1.56 (1H, m, 1×H-15), 1.56 (3H, s, H-14'), 1.00 (3H, d, J 7.0 Hz, H-10'), 0.95 (t, J 7.0 Hz, H-24), 0.91–0.87 (24H, m, 2×SiC(CH$_3$)$_3$, H-18', H-12'), 0.68 (3H, d, J 7.0 Hz, H-16'), 0.09 (3H, s, 1×SiCH$_3$), 0.06 (9H, s, 3×SiCH$_3$); $^{13}$C NMR (100 MHz) δ 166.4, 157.1, 152.3, 132.7, 132.0, 130.2, 130.0, 118.4, 80.5, 78.9, 76.9, 50.8, 37.9, 37.4, 35.8, 35.1, 33.8, 26.1, 22.8, 20.7, 18.4, 18.2, 17.8, 14.4, 13.9, 10.0, −3.4, −3.6, −3.7; mass spectrum m/z 718 [M+Na]$^+$, 564 [M-OTBDMS]$^+$, 495 (Found: [M+Na]$^+$, 718.4894. C$_{38}$H$_{73}$NO$_6$Si$_2$ requires [M+Na]$^+$, 718.4990).

To a solution of carbamoylated methyl ester 40 (0.277 g, 0.40 mmol, 1.0 eq) in CH$_2$Cl$_2$ (6.0 ml) at −78° C. was added diisobutylaluminium hydride (3.12 ml of a 1.0M solution in hexane, 3.12 mmol, 8.0 eq). The solution was stirred at −78° C. for 25 minutes before transferring to a solution of Rochelle's salt (25 ml) at 0° C. via canula. The mixture was stirred for 1.5 hours before partitioning and extracting the aqueous phase with CH$_2$Cl$_2$ (3×25 ml). The combined organic phases were dried (Na$_2$SO$_4$) and concentrated under reduced pressure. Column chromatography (silica, 30% EtOAc-hexane) yielded allylic alcohol 21 (0.234 g, 88%) as a colourless oil; $^1$H NMR (400 MHz) δ 5.60–5.54 (2H, m, H-9, H-8), 5.41–5.35 (1H, m, H-22), 5.23 (1H, t, J 10.5 Hz, H-21), 4.97 (1H, d, J 10.0 Hz, H-13), 4.77 (2H, br s, NH$_2$), 4.69 (1H, t, J 6.0 Hz, H-19), 4.12–4.08 (2H, m, 2×H-7), 3.36 (1H, dd, J 5.0, 4.0 Hz, H-17), 3.24 (1H, dd, J 7.0, 3.0 Hz, H-11), 2.81–2.76 (1H, m, H-20), 2.63 (1H, m, H-10), 2.41–2.35 (1H, m, H-12), 2.16–1.99 (3H, m, 2×H-23, H-15), 1.88–1.85 (2H, m, H-18, H-16), 1.67 1H, m, 1×H-15), 1.61 (3H, s, H-14'), 0.99–0.88 (15H, m, H-24, H-20', H-18', H-12', H-10'), 0.91 (9H, s, SiC(CH$_3$)$_3$), 0.90 (9H, s, SiC(CH$_3$)$_3$), 0.70 (3H, d, J 6.5 Hz, H-16'), 0.08 (3H, s, 1×SiCH$_3$), 0.07 (3H, s, 1×SiCH$_3$), 0.04 (6H, s, 2×SiCH$_3$); $^{13}$C NMR MHz) δ 157.2, 134.8, 132.5, 132.1, 130.7, 130.4, 128.3, 80.7, 78.8, 58.8, 38.1, 37.0, 36.5, 36.4, 34.8, 33.8, 26.2, 22.8, 20.8, 19.2, 18.4, 17.7, 14.4, 13.4, 10.1, −3.5, −3.6, −3.7; mass spectrum m/z 690 [M+Na]$^+$, 536, 404 (Found: [M+Na]$^+$, 690.4930. C$_{37}$H$_{73}$NO$_5$Si$_2$ requires [M+Na]$^+$, 690.4920).

To a solution of allylic alcohol 41 (0.234 g, 0.351 mmol, 1.0 eq) in CH$_2$Cl$_2$ (5.0 ml) was added NaHCO$_3$ (0.059 g, 0.702 mmol, 2.0 eq) followed by Dess-Martin periodane (0.179 g, 0.421 mmol, 1.2 eq). The solution was stirred at room temperature for 30 minutes before adding NaHCO$_3$—Na$_2$S$_2$O$_3$ (1:1, 20 ml). The organic phases were extracted with CH$_2$Cl$_2$ (3×20 ml), combined, and dried (Na$_2$SO$_4$) before concentration under reduced pressure. Column chromatography (silica, 30% EtOAc-hexane) yielded aldehyde 25 (0.2304 g, 87%) as a white solid; $^1$H NMR (400 MHz) δ 9.82 (1H, d, J 8.5 Hz, CHO), 6.71 (1H, t, J 11.0 Hz, H-9), 5.88 (1H, dd, J 11.0, 8.5 Hz, H-8), 5.38–5.34 (1H, m, H-22), 5.27 (1H, dd, J 10.5, 10.0 Hz, H-21), 4.93 (1H, d, J 11.0 Hz, H-13), 4.74 (2H, br s, NH$_2$), 4.69 (1H, t, J 6.0 Hz, H-19), 3.43–3.32 (3H, m, H-17, H-11, H-10), 2.77 (1H, m, H-20), 2.29 (1H, m, H-12), 2.07–1.98 (3H, m, 2×H-23, 1×H-15), 1.88–1.80 (2H, m, H-18, H-16), 1.59 (3H, s, H-14'), 1.49 (1H, d, J 12.0 Hz, 1×H-15), 1.08 (3H, d, J 7.0 Hz, H-10'), 0.99–0.87 (9H, m, H-20', H-18', H-12'), 0.92 (9H, s, SiC(CH$_3$)$_3$), 0.90 (9H, s, 1×SiC(CH$_3$)$_3$), 0.68 (3H, d, J 7.0 Hz, H-16'), 0.08 (3H, s, 1×SiCH$_3$), 0.07 (6H, s, 2×SiCH$_3$), 0.04 (3H, s, 1×SiCH$_3$); $^{13}$C NMR MHz) δ 191.0, 157.0, 154.8, 133.8, 132.0, 130.4, 129.6, 129.2, 80.4, 78.4, 38.2, 38.0, 36.6, 36.4, 34.5, 33.9, 26.1, 22.7, 20.7, 19.5, 18.4, 17.7, 14.4, 13.4, 16.3, −3.2, −3.4, −3.6; mass spectrum m/z 688 [M+Na]$^+$ (Found: [M+Na]$^+$, 688.4706. C$_{37}$H$_{71}$NO$_5$Si$_2$ requires [M+Na]$^+$, 688.4763).

EXAMPLE 11

Levulinic acid Weinreb amide 22, used as a synthon in the preparation of compounds III-A and III-B, was prepared as shown below:

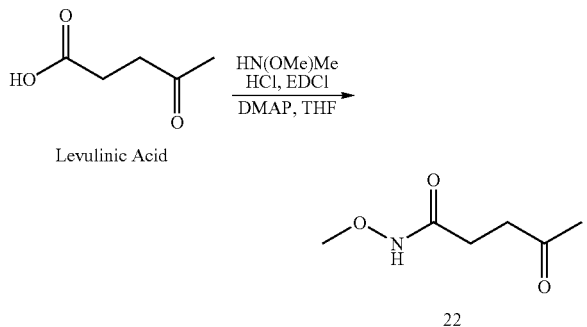

Levulinic Acid

To a solution of levulinic acid (1 eq) in THF was added N,O-dimethylhydroxylamine hydrochloride (2 eq) and dimethylaminopyridine ("DMAP", 2 eq) followed by (3-dimethylamino)propylethylcarbodiimide ("EDCL", 2 eq). The solution was stirred at room temperature for 14 hours before partitioning between EtOAc and NaHCO$_3$. The aqueous phase was extracted with EtOAc (2×) and the combined organic phases dried (Na$_2$SO$_4$) before concentration under reduced pressure. Column chromatography (silica, 70% EtOAc-hexane) yielded Weinreb amide 22 as a colorless oil; $^1$H NMR (400 MHz) δ 9.82 3.71 (3H, s, NOCH$_3$), 3.16 (3H, s, NCH$_3$), 2.74 (2H, d, J 5.5 Hz, 1×CH$_2$), 2.70 (2H, m, 1×CH$_2$), 2.19 (3H, s, COCH$_3$).

Those skilled in the art will appreciate that other compounds III can be made by generally following the methods described in the preceding examples, *mutatis mutandis*. For instance, compounds in which R$^{22}$ is H can be made by using, as a starting material, counterparts of compounds 21 or 25 where the corresponding CH$_3$ has been replaced by H. The preparation of discodermolide compounds and intermediates therefor where such a replacement has been effected is disclosed in Smith, III, et al., US 2004/0048894 A1 (2004), the disclosure of which is incorporated herein by reference. Similarly, compounds in which R$^{21}$ is CH$_3$ can be prepared by using, as starting materials, counterparts of compounds 21 or 25 bearing a CH$_3$ at the appropriate location. Compounds in which the C$_{23}$–C$_{24}$ double bond is hydrogenated (i.e., R$^{23}$ and R$^{24}$ are each H) also can be made by selective hydrogenation, as disclosed in Gunasekera et al., U.S. Pat. No. 4,939,168 (1990), the disclosure of which is incorporated herein by reference.

EXAMPLE 12

The biological activity of compounds III was evaluated by measuring their inhibitory effect on the proliferation of various tumor cell lines. Results, including comparative ones for discodermolide, are tabulated in Table 3. The characteristics of the cells lines used has been described hereinabove.

TABLE 3

| Compound | Tumor Cell Line (IC$_{50}$, nM)* | | | |
|---|---|---|---|---|
| | MCF-7 | NCI/ADR | A549 | SKOV-3 |
| Discodermolide | 14.1 | 247 | 24.4 | 31.7 |
| III-A | 2.9 | 350 | 4.9 | 14 |
| III-B | 6.4 | 730 | 46 | 15 |

*Some results are the average of multiple runs.

EXAMPLE 13

The synthesis of compound IV-A is shown schematically in FIG. 6.

To a solution of diisopinocamphylene boron chloride ("DiP-Cl", 0.089 g, 2.79 mmol, 8.0 eq) in diethyl ether (1.0 mL) at 0° C. was added triethylamine (0.043 mL, 3.07 mmol, 8.8 eq) forming a milky solution to which was added a solution of methyl ketone 52a (Kinder, Jr. et al., U.S. Pat. No. 6,506,910 B1 (2003), incorporated herein by reference; 0.065 g, 2.79 mmol, 8.0 eq) in ether (1.0 mL). After stirring at 0° C. for 1 hour the solution was cooled to −78° C. and a solution of aldehyde 51 (0.023 g, 0.34 mmol, 1.0 eq) was added as a solution in ether (1.0 mL). The solution was stirred at −78° C. for 3 hours and placed at −20° C. for 16 hours. After warming to 0° C., MeOH (1.0 mL) was added followed by phosphate buffer (pH 7, 1.0 mL of a 1.0M solution) and hydrogen peroxide (0.5 mL of a 30% solution in water). The mixture was stirred at room temperature for 1 hour before diluting with water (10 mL) and extracting the organics with CH$_2$Cl$_2$ (3×15 mL). The combined organic phases were dried (Na$_2$SO$_4$) and concentrated under reduced pressure. Column chromatography (silica, 40% EtOAc-hexane) yielded β-hydroxyketone 53a (0.027 g, 87%) as a colourless oil; $^1$H NMR (400 MHz) δ 5.43 (1H, t, J 10.5 Hz, H-9), 5.39–5.31 (2H, m, H-22, H-8), 5.26 (1H, m, H-21), 5.00 (1H, d, J 9.5 Hz, H-13), 5.00 (1H, m, H-7), 4.69 (3H, m, H-19, NH$_2$), 3.74–3.71 (1H, m, H-3), 3.72 (3H, s, NOCH$_3$), 3.37 (1H, dd, J 5.0, 4.0 Hz, H-17), 3.32 (3H, s, OCH$_3$), 3.27 (1H, dd, J 5.5, 5.0 Hz, H-11), 3.17 (3H, s, NCH$_3$), 3.00 (1H, m, H-4 or H-2), 2.82–2.78 (2H, m, H-20, H-4 or H-2), 2.69 (1H, m, H-10), 2.65 (2H, d, J 6.0 Hz, 2×H-6), 2.41 (1H, m, 5H-12), 2.08–1.99 (2H, m, 2×H-23), 1.87 (3H, m, H-18, H-16, 1×H-15), 1.62 (1H, m, 1×H-15), 1.59 (3H, s, H-14'), 1.15 (3H, d, J 7.0 Hz, H-4' or H-2'), 1.06 (3H, d, J 7.0 Hz, H-4' or H-2'), 0.98 (3H, d, J 7.0 Hz, H-10'), 0.97 (3H, t, J 7.5 Hz, H-24), 0.94–0.88 (9H, m, H-20', H-18', H-12'), 0.91 (9H, s, 1×SiC(CH$_3$)$_3$), 0.90 (9H, s, 1×SiC(CH$_3$)$_3$), 0.70 (3H, d, J 6.5 Hz, H-16'), 0.09 (3H, s, 1×SiCH$_3$), 0.07 (3H, s, 1×SiCH$_3$), 0.03 (3H, s, 1×SiCH$_3$), 0.02 (3H, s, 1×SiCH$_3$); $^{13}$C NMR (100 MHz) δ 213.8, 156.9, 135.7, 132.0, 131.0, 130.4, 129.5, 84.0, 80.6, 78.6, 77.1, 64.3, 61.2, 60.2, 49.7 (2C), 37.9, 37.7, 37.1, 36.4, 36.2, 34.7, 33.8, 26.2 (2C), 22.9, 20.8, 18.7, 18.5, 18.4, 17.7, 16.9, 14.4, 13.4, 12.9, 12.0, 10.2, −3.2, −3.4 (2C), −3.9; mass spectrum m/z 920 [M+Na]$^+$, 748, 716 (Found: [M+Na]$^+$, 919.6199. C$_{48}$H$_{92}$N$_2$O$_9$Si$_2$ requires [M+Na]$^+$, 919.6234).

To a solution of the tetramethylammonium triacetoxyborohydride (0.073 g, 0.278 mmol, 10.0 eq) in acetonitrile (0.5 mL) was added glacial acetic acid (0.5 mL). After stirring at room temperature for 30 minutes, the solution was cooled to −30° C. and a precooled solution of ketone 53a (0.025 g, 0.028 mmol, 1.0 eq) in acetonitrile-acetic acid (1:1, 2 mL) was added. The solution was stirred at −30° C. for 30 minutes and 0° C. for a further 1 hour before adding a solution of Rochelle's salt (7 mL) and stirring for 5 minutes. The mixture was partitioned between NaHCO$_3$ (20 mL) and CH$_2$Cl$_2$ (20 mL) and the aqueous phase extracted with CH$_2$Cl$_2$ (3×15 mL). The combined organic phases were dried (Na$_2$SO$_4$) and concentrated under reduced pressure. Column chromatography (silica, 35 to 50% EtOAc-hexane gradient) yielded the anti diol 54a (0.020 g, 81%) as a colourless oil; $^1$H NMR (400 MHz) δ 5.94 (1H, dd, J 11.0, 9.5 Hz, H-9), 5.43–5.35 (2H, m, H-22, H-8), 5.26 (1H, dd, J 11.0, 10.0 Hz, H-21), 4.99 (1H, d, J 10.5 Hz, H-13), 4.70 (1H, t, J 6.0 Hz, H-19), 4.64 (3H, m, H-7, NH$_2$), 3.72 (3H, s, NOCH$_3$), 3.62–3.57 (2H, m, H-5, H-2), 3.44 (3H, s, OCH$_3$), 3.37 (1H, dd, J 5.0, 4.0 Hz, H-17), 3.28 (1H, dd, J 6.5, 3.5 Hz, H-11), 3.20 (3H, s, NCH$_3$), 3.14 (1H, m, H-2), 2.79 (1H, m, H-20), 2.71 (1H, m, H-10), 2.42 (1H, m, H-12), 2.15–2.00 (3H, m, 2×H-23, 1×H-15), 1.90–1.86 (3H, m, H-18, H-16, H-4), 1.75–1.63 (3H, m, 2×H-6, 1×H-15), 1.60 (3H, s, H-14'), 1.22 (3H, d, J 7.0 Hz, H-2'), 1.00–0.84 (18H, m, H-24, H-20', H-18', H-12', H-10', H-4'), 0.92 (9H, s, 1×SiC(CH$_3$)$_3$), 0.90 (9H, s, 1×SiC(CH$_3$)$_3$), 0.71 (3H, d, J 6.5 Hz, H-16'), 0.09 (3H, s, 1×SiCH$_3$), 0.07 (3H, s, 1×SiCH$_3$), 0.04 (3H, s, 1×SiCH$_3$), 0.03 (3H, s, 1×SiCH$_3$); $^{13}$C NMR (100 MHz) δ 157.0, 134.2, 132.0 (2C), 131.4, 131.1, 130.4, 84.6, 80.6, 78.6, 77.1, 70.7, 65.4, 61.5, 59.7, 41.9, 40.5, 37.9, 37.1, 36.4 (2C), 34.7, 33.8, 32.4, 26.2, 22.9, 20.7, 18.9, 18.5, 18.4, 17.7, 17.2, 14.5, 14.4, 10.1, −3.3, −3.4 (2C), −4.0; mass spectrum m/z 922 [M+Na]$^+$, 882 (Found: [M+Na]$^+$, 921.6358. C$_{48}$H$_{94}$N$_2$O$_9$Si$_2$ requires [M+Na]$^+$, 921.6390).

Removal of the t-butyldimethylsilyl protective groups from anti diol 54a and lactonization were effected in a combined step. To a solution of anti diol 54a (0.016 g, 0.018 mmol, 1.0 eq) in methanol (3.0 mL) at room temperature was added hydrochloric acid (4.5M, 2×1.0 mL aliquots) over a period of 60 minutes. After stirring at room temperature for a further 2 hours, the solution was diluted with CH$_2$Cl$_2$ (15 mL) and neutralized with NaHCO$_3$ (10 mL). The aqueous phase was extracted with CH$_2$Cl$_2$ (3×10 mL) and the combined organics dried (Na$_2$SO$_4$) and concentrated under reduced pressure. Column chromatography (silica, 7% MeOH—CH$_2$Cl$_2$) yielded compound IV-A (0.010 g, 92%) as a colourless oil; $^1$H NMR (400 MHz) δ 5.51 (1H, dd, J 11.0, 8.0 Hz, H-8), 5.41–5.36 (2H, m, H-22, H-9), 5.26 (1H, t, J 10.5 Hz, H-21), 5.18 (1H, d, J 9.0 Hz, H-13), 4.76–4.72 (3H, m, H-7, NH$_2$), 4.69 (1H, dd, J 6.5, 4.5 Hz, H-19), 4.59 (1H, dt, J 8.5, 1.0 Hz, H-5), 3.37 (3H, s, OCH$_3$), 3.25 (1H, br t, J 7.0 Hz, H-17), 3.20–3.16 (2H, m, H-11, H-3), 2.86–2.75 (3H, m, H-20, H-10, H-2), 2.62–2.57 (1H, m, H-12), 2.20–1.96 (5H, m, 2×H-23, H-18, H-16, H-4), 1.94–1.80 (3H, m, 2×H-15, 1×H-6), 1.68 (1H, dd, J 10.5, 2.5 Hz, 1×H-6), 1.66 (3H, s, H-14'), 1.29 (3H, d, J 7.0 Hz, H-2'), 1.04 (3H, d, J 7.0 Hz, H-4'), 1.00 (3H, d, J 7.0 Hz, H-18'), 0.98–0.93 (12H, m, H-24, H-20', H-12', H-10'), 0.83 (3H, d, J 5.5 Hz, H-16'); $^{13}$C NMR (100 MHz) δ 173.8, 157.2, 134.2, 133.2, 132.9, 132.2, 130.3, 129.7, 82.4, 79.0, 78.8, 77.9, 75.8, 64.2, 57.6, 41.3, 39.0, 37.3, 36.1, 35.8, 35.0, 34.2, 33.9, 33.0, 23.2, 20.7, 18.1, 17.8, 16.0, 15.3, 14.4, 13.9, 12.9, 8.9; mass spectrum m/z 633 [M+Na]$^+$, 610 [M+H]$^+$, 532, 293 (Found: [M+Na]$^+$, 632.4150. C$_{34}$H$_{59}$NO$_8$ requires [M+Na]$^+$, 632.4133).

EXAMPLE 14

As with compound IV-A, the synthesis of compound IV-B is summarized schematically in FIG. 6.

Using a similar procedure to that above for the preparation of β-hydroxyketone 53a, aldehyde 51 and methyl ketone 52b (Kinder, Jr. et al., U.S. Pat. No. 6,506,910 B1 (2003), incorporated herein by reference) were reacted on a 0.018 mmol scale to yield β-hydroxyketone 53b (0.013 g, 83%) as a colourless oil; $^1$H NMR (400 MHz) δ 5.46 (1H, t, J 11.0 Hz, H-9), 5.40–5.34 (2H, m, H-22, H-8), 5.28 (1H, m, H-21), 4.98 (1H, d, J 10.0 Hz, H-13), 4.74–4.67 (2H, m, H-19, H-7), 4.61 (2H, br s, NH$_2$), 3.66 (3H, s, NOCH$_3$), 3.37 (1H, t, J 4.0 Hz, H-17), 3.29 (1H, dd, J 7.0, 4.0 Hz, H-11), 3.17 (3H, s, NCH$_3$), 2.95 (1H, m, H-4 or H-2), 2.81 (1H, m, 1H of H-20, H-4 or H-2), 2.67–2.49 (4H, m, 4H of H-20, H-10, 2×H-6, H-4, H-2), 2.42 (1H, m, H-12), 2.13–2.02 (3H, m, 2×H-23, 1×H-3), 1.90–1.72 (4H, m, H-18, H-16, 1×H-15, 1×H-3), 1.67 (1H, m, 1×H-15), 1.62 (3H, s, H-14'), 1.10 (3H, d, J 7.0 Hz, H-4' or H-2'), 1.07 (3H, d, J 7.0 Hz, H-4' or H-2'), 0.98 (3H, t, J 7.5 Hz, H-24), 0.95–0.88 (12H, m, H-20', H-18', H-10', H-12'), 0.92 (9H, s, 1×SiC(CH$_3$)$_3$), 0.91 (9H, s, 1×SiC(CH$_3$)$_3$), 0.71 (3H, d, J 7.0 Hz, H-16'), 0.09 (3H, s, 1×SiCH$_3$), 0.08 (3H, s, 1×SiCH$_3$), 0.04 (6H, s, 2×SiCH$_3$); mass spectrum m/z 890 [M+Na]$^+$, 850, 718.

The reduction of β-hydroxyketone 53b was carried out of a 0.015 mmol scale and the crude product diol 54b was used in the next step without purification.

The simultaneous deprotection and lactonization of diol 54b was carried out on a 0.015 mmol scale in the same manner as described above for diol 54a to yield a mixture of the ring opened methyl ester and compound IV-B (0.0005 g, 6% over two steps); $^1$H NMR MHz) δ 5.52 (1H, dd, J 11.5, 7.0 Hz, H-9), 5.44–5.37 (2H, m, H-22, H-8), 5.26 (1H, dd, J 11.0, 9.5 Hz, H-21), 5.18 (1H, d, J 9.5 Hz, H-13), 4.74–4.70 (5H, m, H-19, H-7, H-5, NH$_2$), 3.26 (1H, m, H-17), 3.20 (1H, m, H-11), 2.82 (2H, m, 2H of H-20, H-12, H-10, H-2), 2.64 (2H, m, 2H of H-20, H-12, H-10, H-2), 2.10–1.63 (H, m, 2×H-23, H-18, H-16, 2×H15, 2×H-6, H-4, 2×H-3), 1.56 (3H, s, H-14'), 1.21 (3H, d, J 7.0 Hz, H-2'), 1.04–0.94 (18H, H-24, H-20', H-18', H-12', H-10', H-4'), 0.84 (3H, br s, H-16'); mass spectrum m/z 602 [M+Na]$^+$, 430.

Those skilled in the art will appreciate that other compounds IV can be made by generally following the methods described in the preceding examples, *mutatis mutandis*. For instance, compounds in which R$^{33}$ is H can be made by using counterpart starting materials where the corresponding CH$_3$ has been replaced by H. The preparation of discodermolide compounds and intermediates therefor where such a replacement has been effected is disclosed in Smith, III, et al., US 2004/0048894 A1 (2004), the disclosure of which is incorporated herein by reference. Similarly, compounds in which R$^{32}$ is CH$_3$ can be prepared by using counterpart starting materials bearing a CH$_3$ at the appropriate location. Compounds in which the C$_{23}$–C$_{24}$ double bond is hydrogenated (i.e., R$^{34}$ and R$^{35}$ are each H) can be made by selective hydrogenation, as disclosed in Gunasekera et al., U.S. Pat. No. 4,939,168 (1990), the disclosure of which is incorporated herein by reference.

EXAMPLE 15

The biological activity of compounds IV was evaluated by measuring their inhibitory effect on the proliferation of various tumor cell lines. Results, including comparative ones for discodermolide, are tabulated in Table 4. The characteristics of the cell lines used has been discussed hereinabove.

TABLE 4

| Tumor Cell Line | Compound | | |
|---|---|---|---|
| (IC$_{50}$, nM)* | Discodermolide | IV-A | IV-B |
| MCF-7 | 14.1 | 5.8 | 3.8 |
| NCI/ADR | 247 | 140 | 250 |
| A549 | 24.4 | 11 | 6.5 |
| HL-60/MX2 | 150 | 12 | 4.1 |
| CCRF-CEM | 14.8 | 8.6 | 4.4 |
| A549 t12 | 26.7 | 50 | 12 |
| CCRF-CEM/PTX | 92.8 | 65 | 79 |
| CCRF-CEM/VBL | 158 | 209 | 416 |
| CCFR-CEM/VP16 | 53 | 12 | 8.4 |

*Some results are the average of multiple runs.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having a structure represented by formula A:

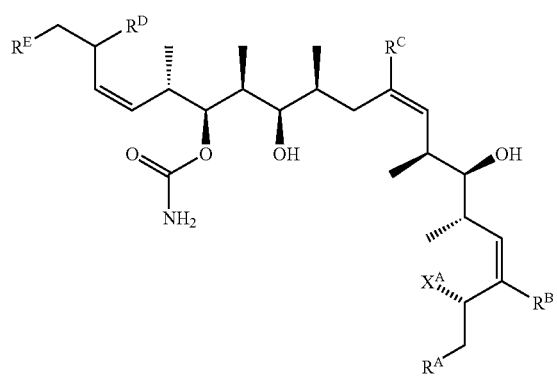

and the pharmaceutically acceptable salts, esters, and solvates thereof
wherein
$R^A$ is

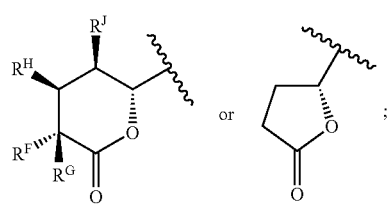

wherein
$R^F$ and $R^J$ are independently H or $CH_3$;
$R^G$ is H;
$R^H$ is H, $OCH_3$, or OH, or $R^H$ combines with $R^G$ to form a bond;
$R^B$ and $R^C$ are independently H or $CH_3$;
$R^D$ and $R^E$ are each H or $R^D$ and $R^E$ combine to form a bond; and
$X^A$ is H or $CH_3(OCH_2CH_2)_nOCH_2O$, where the subscript n is 0 or 1;

subject to the proviso that at least one of the following conditions is satisfied:
(a) $R^B$ is $CH_3$;
(b) $X^A$ is $CH_3(OCH_2CH_2)_nOCH_2O$, where the subscript n is 0 or 1; or
(c) $R^A$ is

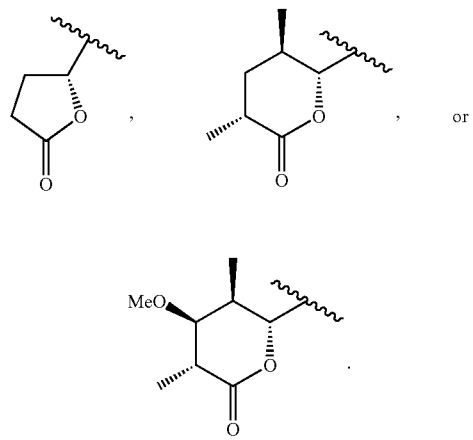

2. A compound according to claim 1, having a structure represented by formula I:

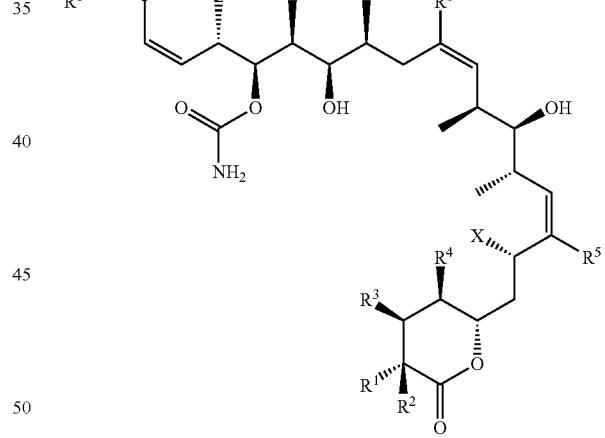

and the pharmaceutically acceptable salts esters, and solvates thereof
wherein
$R^1$, $R^4$, $R^5$, and $R^6$ are independently H or $CH_3$;
$R^2$ is H;
$R^3$ is H or OH, or $R^3$ combines with $R^2$ to form a bond;
$R^7$ and $R^8$ are each H or $R^7$ and $R^8$ combine to form a bond; and
X is $CH_3(OCH_2CH_2)_nOCH_2O$, where the subscript n is 0 or 1.

3. A compound according to claim 2, represented by formula Ib:

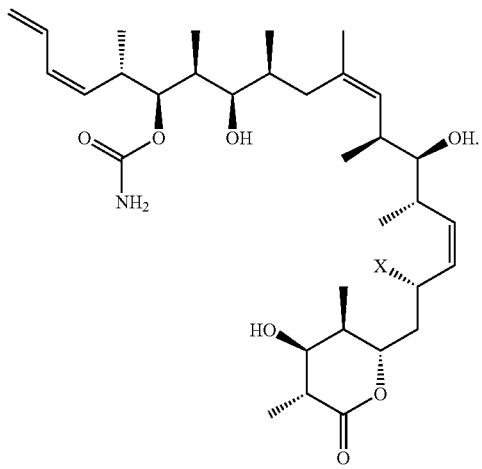

(Ib)

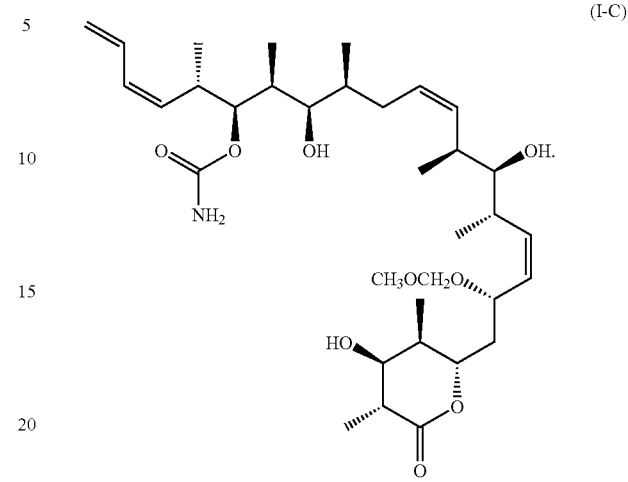

(I-C)

-continued

4. A compound according to claim 2, represented by formula I-A, I-B, or I-C:

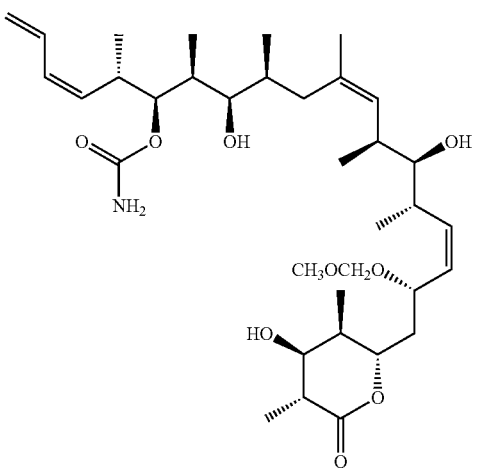

(I-A)

5. A compound according to claim 1, having a structure represented by formula II

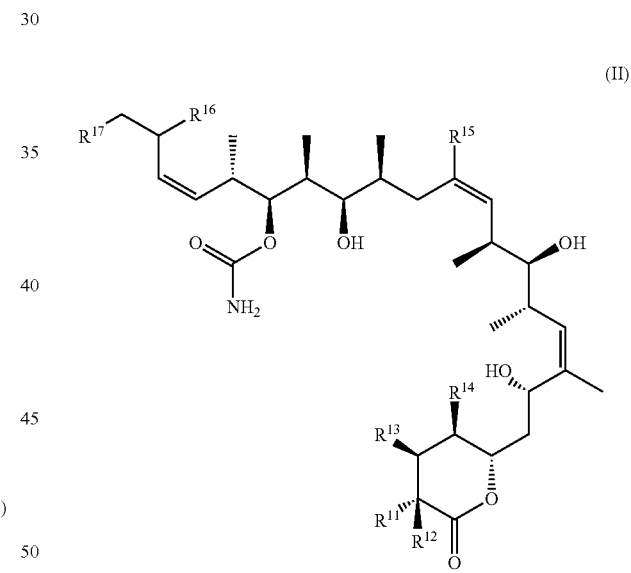

(II)

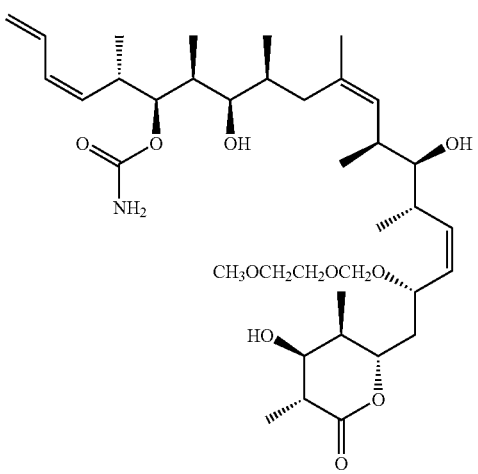

(I-B)

and the pharmaceutically acceptable salts esters, solvates thereof
wherein
  $R^{11}$, $R^{14}$, and $R^{15}$ are independently H or $CH_3$;
  $R^{12}$ is H;
  $R^{13}$ is H or OH, or $R^{13}$ combines with $R^{12}$ to form a bond; and
  $R^{16}$ and $R^{17}$ are each H or $R^{16}$ and $R^{17}$ combine to form a bond.

6. A compound according to claim 5, having a structure represented by formula II-A:

(II-A)

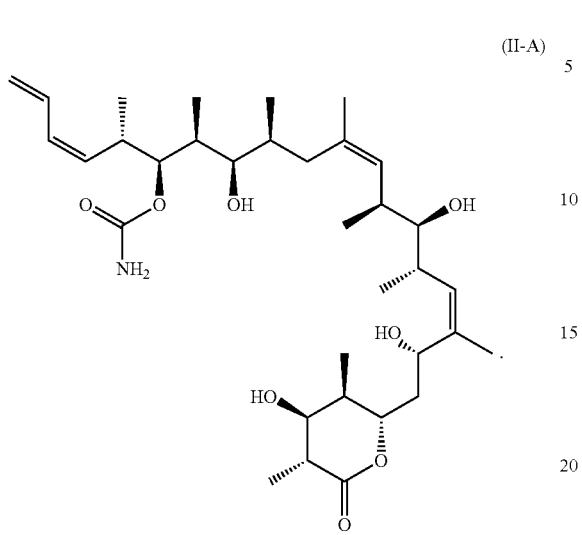

7. A compound according to claim 1, having a structure represented by formula III (III)

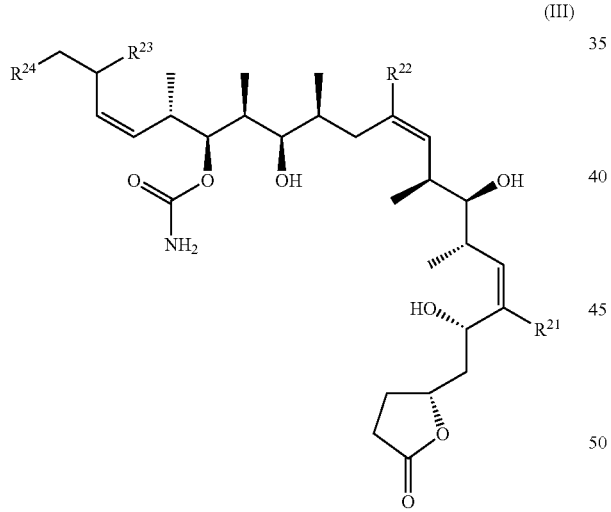

and the pharmaceutically acceptable salts esters, and solvates thereof
wherein
$R^{21}$ and $R^{22}$ are independently H or $CH_3$; and
$R^{23}$ and $R^{24}$ are each H or $R^{23}$ and $R^{24}$ combine to form a bond.

8. A compound according to claim 7, having a structure represented by formula III-A or III-B:

(III-A)

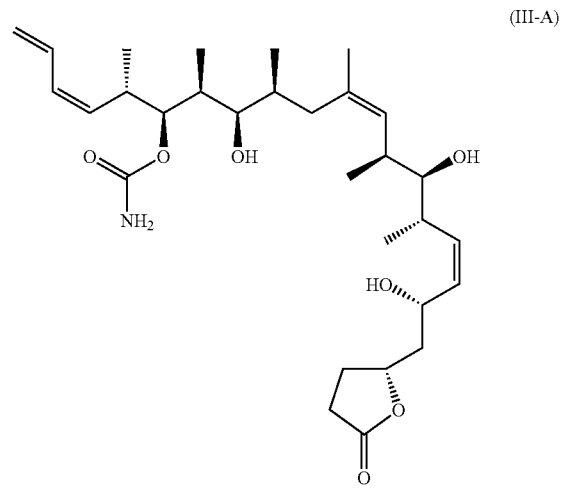

(III-B)

9. A compound according to claim 1, having a structure represented by formula IV (IV)

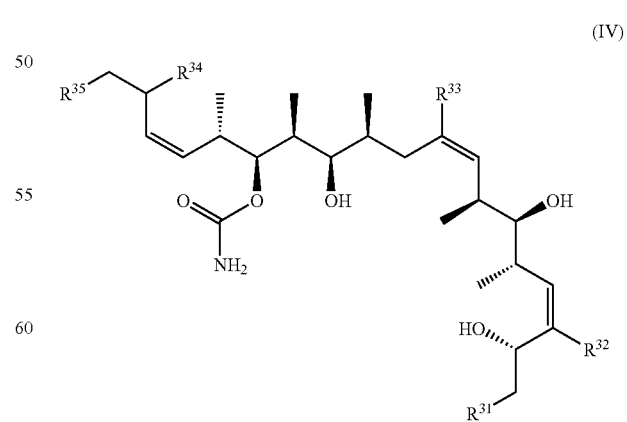

and the pharmaceutically acceptable salts, esters, solvates thereof wherein
$R^{31}$ is

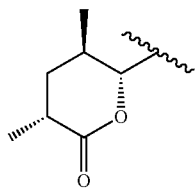, or 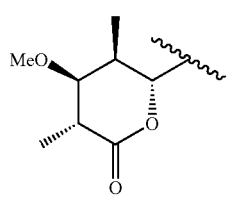;

$R^{32}$ and $R^{33}$ are independently H or $CH_3$; and
$R^{34}$ and $R^{35}$ are each H or $R^{34}$ and $R^{35}$ combine to form a bond.

10. A compound according to claim 9, having a structure represented by formula IV-A, or IV-B

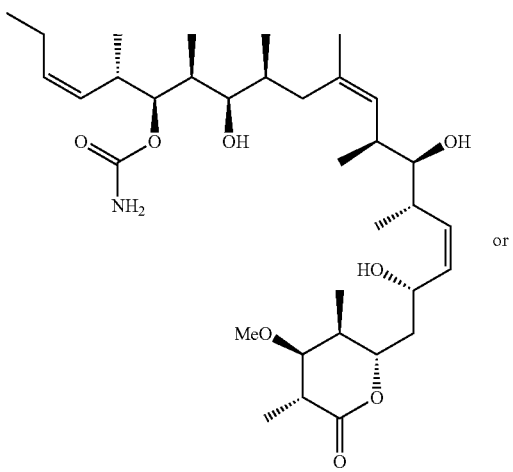

(IV-A)

or

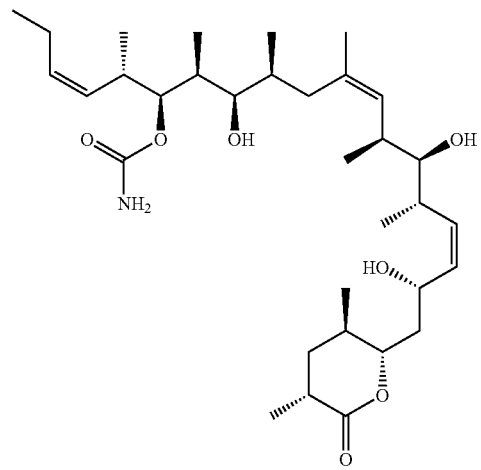

(IV-B)

11. A method of inhibiting the proliferation of a target cell that is a breast cancer, lung cancer, ovary cancer, or leukemia cell, comprising contacting the target cell with an effective amount of a compound according to claim 1.

12. A method according to claim 11, wherein the compound is the compound of claim 2.

13. A method according to claim 11, wherein the compound is the compound of claim 5.

14. A method according to claim 11, wherein the compound is the compound of claim 7.

15. A method according to claim 11, wherein the compound is the compound of claim 9.

16. A method of treating a hyperproliferative disease selected from the group consisting of breast cancer, lung cancer, ovary cancer, and leukemia, comprising administering to a patient suffering from such hyperproliferative disease a therapeutically effective amount of a compound according to claim 1.

17. A method according to claim 16, wherein the compound is the compound of claim 2.

18. A method according to claim 16, wherein the compound is the compound of claim 5.

19. A method according to claim 16, wherein the compound is the compound of claim 7.

20. A method according to claim 16, wherein the compound is the compound of claim 9.

* * * * *